US010858410B2

(12) United States Patent
Polt et al.

(10) Patent No.: US 10,858,410 B2
(45) Date of Patent: Dec. 8, 2020

(54) GLYCOSYLATED PEPTIDES WITH PSEUDOPROLINE RESIDUES AND HAVING ENHANCED HALF-LIVES AND ABILITY TO CROSS THE BLOOD BRAIN BARRIER

(71) Applicant: ARIZONA BOARD OF REGENTS ON BEHALF OF THE UNIVERSITY OF ARIZONA, Tucson, AZ (US)

(72) Inventors: Robin Polt, Tucson, AZ (US); Evan M. Jones, Tucson, AZ (US); Bobbi Anglin, Tucson, AZ (US); Michael L. Heien, Tucson, AZ (US); John M. Streicher, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 15/752,157

(22) PCT Filed: Aug. 12, 2016

(86) PCT No.: PCT/US2016/046900

§ 371 (c)(1),
(2) Date: Feb. 12, 2018

(87) PCT Pub. No.: WO2017/027848

PCT Pub. Date: Feb. 16, 2017

(65) Prior Publication Data

US 2020/0270318 A1 Aug. 27, 2020

Related U.S. Application Data

(60) Provisional application No. 62/204,351, filed on Aug. 12, 2015, provisional application No. 62/204,371, filed on Aug. 12, 2015.

(51) Int. Cl.
*A61K 38/00* (2006.01)
*C07K 14/47* (2006.01)

(52) U.S. Cl.
CPC .................................. *C07K 14/473* (2013.01)

(58) Field of Classification Search
None
See application file for complete search history.

(56) References Cited

U.S. PATENT DOCUMENTS 7,183,261 B2 2/2007 Uematsu et al.
2010/0256333 A1 10/2010 Zhang et al.
2010/0291089 A1 11/2010 Kim et al.
2011/0288011 A1* 11/2011 Castaigne ................ A61P 1/04 514/5.3
2016/0016996 A1 1/2016 Hay et al.
2016/0206681 A1 7/2016 Hay et al.
2017/0304391 A1 10/2017 Hay et al.

FOREIGN PATENT DOCUMENTS

WO WO2015002903 A1 1/2015
WO WO2015023890 A1 2/2015

OTHER PUBLICATIONS

Cheng et al. Neuroprotection of a Novel Cyclopeptide C*HSDGIC* from the Cyclization of PACAP (1-5) in Cellular and Rodent Models of Retinal Ganglion Cell Apoptosis. 2014. PLOS ONE 9(10): e108090. https://doi.org/10.1371/journal.pone.0108090.
Fahmi et al. "Site-Specific Incorporation of Glycosylated Serine and Tyrosine Derivatives into Proteins," Journal of the American Chemical Society, Mar. 6, 2007. vol. 129, pp. 3586-3597.
Forte, BL et al. Angiotensin-(1-7)/Mas receptor as an antinociceptive agent in cancer-induced bone pain. Pain 157, 2709-2721 (2016).
Mitchell et al., Solid-Phase Synthesis of O-Linked Glycopeptide Analogues of Enkephalin. J. Org. Chem. 66, 2327-2342 (2001).
Polt et al., General Methods for α- or β-O-Ser/Thr Glycosides and Glycopeptides. Solid-Phase Synthesis of O-Glycosyl Cyclic Enkephalin Analogues. J. Am. Chem. Soc. 114, 10249-10258 (1992).
Robberecht et al., Structural requirements for the occupancy of pituitary adenylate-cyclase-activating peptide (PACAP) receptors and adenylate cyclase activation in human neuroblastoma NB-OK-1 cell membranes. Discovery of PACAP6-38 as a potent antagonist. Eur. J. Biochem. 1992, 207, 239-246.
Villela, DC, Passos-Silva, DG, and Santos, RAS . . . Alamandine: a new member of the angiotensin family. Curr. Opin. Nephrol. Hypertens. 23, 130-134 (2014).

* cited by examiner

*Primary Examiner* — Jeanette M Lieb
(74) *Attorney, Agent, or Firm* — Nguyen Tarbet LLC

(57) ABSTRACT

Glycosylated peptides with glycosylation at or near the C-terminal domain of the peptide have an enhanced ability to cross the blood brain barrier (BBB) and/or enhanced half-lives. These glycosylated peptides may be used as drugs. For example, a PACAP peptide with a C-terminal glycosylation, e.g., in lieu of the terminal leucine, functions as a $PAC_1$ agonist with enhanced ability to cross the BBB and with enhanced half-life. The peptides can have a pseudoproline residue with glycosylation at or near the C-terminal domain.

18 Claims, 6 Drawing Sheets
(3 of 6 Drawing Sheet(s) Filed in Color)
Specification includes a Sequence Listing.

Angiotensin$_{1-7}$

PN-A5

GLYCOSYLATED PEPTIDES WITH PSEUDOPROLINE RESIDUES AND HAVING ENHANCED HALF-LIVES AND ABILITY TO CROSS THE BLOOD BRAIN BARRIER

CROSS REFERENCE

This application claims priority to U.S. Provisional Patent Application No. 62/204,371, filed Aug. 12, 2015 and U.S. Provisional Patent Application No. 62/204,351, filed Aug. 12, 2015, the specification(s) of which is/are incorporated herein in their entirety by reference.

GOVERNMENT SUPPORT

This invention was made with government support under Grant Nos. ROI NS052727 awarded by NIH; CHE0607917 awarded by NSF; N00014-05-1-0807 and N00014-02-1-0471 awarded by NAVY/ONR. The government has certain rights in the invention.

REFERENCE TO SEQUENCE LISTING

Applicant asserts that the information recorded in the form of an Annex C/ST.25 text file submitted under Rule 13ter.1(a), entitled UNIA_15_27_PCT_Seq_List_ST25, is identical to that forming part of the international application as filed. The content of the sequence listing is incorporated herein by reference in its entirety.

FIELD OF THE INVENTION

The present invention relates to peptides used as drugs, more particularly to glycosylated peptides with glycosylation at or near the C-terminus. The glycosylated peptides have enhanced ability to cross the blood brain barrier (BBB) and/or enhanced half-lives. The present invention further relates to glycosidic peptides, in particular, to glycosidic peptides having a pseudoproline residue.

BACKGROUND OF THE INVENTION

Parkinson's disease (PD) is an idiopathic neurological disorder that affects over 2% of the population aged 65 years and older in which the dopaminergic (DA) neurons of the substantia nigra pars compacta (SNc) degenerate. To date, there is no cure for this progressive disease, and the cause of PD remains unclear. Environmental and genetic risk factors, as well as inflammation all play important roles. For familial PD cases, an association with specific genetic mutations is known; these cases share both symptoms and treatment strategies with >90% of PD patients with unknown etiology. The most common familial PD gene mutations, misfolded alpha-synuclein and autophosphorylated leucine-rich repeat kinase 2 (LRRK2) promote the activation of microglia, suggesting inflammatory involvement. Current therapies of PD utilize dopamine-replacement strategies, and do not address the underlying issue of neurodegeneration; they neither slow nor halt disease progression.

A variety of neurotrophic factors, e.g. glial cell-derived neurotrophic factors (GDNF)-family, have shown much promise in preclinical studies, demonstrating robust effects in rodent and primate models. Initial clinical trials of neurotrophic factors have been disappointing, and may reflect sub-optimal dosing, and delivery methods that may not penetrate the blood-brain barrier (BBB). Other peptide neuromodulators may be useful; both vasoactive intestinal peptide (VIP) and the closely related pituitary adenylate cyclase activating peptide (PACAP, Table 1) are potententially neurotrophic and/or neuroprotective peptides, suggesting use as a therapy for PD (Reglodi, et al., 2011). $PACAP_{1-38}$ is known to regulate the development, maintenance, function and plasticity of the neurons, and has been shown to modulate catecholamine storage and exocytosis in PC12 cells. Nerve growth factor (NGF) produces neurite-like process outgrowth similar to what has been observed with PACAP activation. The invention features glycosylated PACAP analogues that can penetrate the BBB in mice at higher rates than expected, which could represent a significant advance in CNS drug design.

Interest in PACAP antagonists stems from reports that $PACAP_{1-38}$ triggers migraine attacks in healthy volunteers and in migraineurs. Since $VPAC_{1\&2}$ receptors may be involved with vasodilation within the brain, there are manifold reasons to develop a deeper understanding of the activity of both agonists and antagonists at PACAP receptors. PACAP antagonists could be beneficial in the treatment of migraine, and glycosylation of PACAP antagonist peptides could also improve CNS drug delivery.

Both $PACAP_{1-38}$ and $PACAP_{1-27}$ bind to and activate the $PAC_1$, $VPAC_1$ and $VPAC_2$ receptors of the secretin family of GPCRs. These three receptors are pleiotropic and widely distributed in the CNS and periphery. The 38 amino acid peptide has higher affinity for the receptors, but both forms activate the receptors with similar potencies. VIP is a 28 amino acid peptide that has 68% identity with $PACAP_{1-27}$ and activates the $VPAC_1$ and $VPAC_2$ receptors equally to both PACAP ligands, but is several orders of magnitude less active at the $PAC_1$ receptor. Native VIP has been shown to form aggregates in aqueous solution and displays surfactant properties at physiological concentrations in vitro. It is possible that both PACAP and VIP interact strongly with biological membranes, and likely promotes the kinetics of binding once the glycopeptides arrive at the neuronal membrane by reducing the 3-dimensional search for the receptors to a 2-dimensional "membrane search". Example 1 discloses studies with PACAP peptide and glycopeptide agonists and antagonists with the $PAC_1$ receptor expressed in CHO cells, PC12 cells, as well as stability studies and BBB penetration. This glycosylation approach may be promising for delivering PACAP drugs to the CNS for the treatment of PD and migraine.

Clinical studies have shown that congestive heart failure (CHF) results in a significant impairment of both spatial memory and object recognition ability. Biophysical, pharmacological and molecular biology studies have implicated the dorsal hippocampus as necessary and required for the formation and storage of spatial memory Likewise, the perirhinal cortex is known to be critical for object recognition memory and necessary for the discrimination of the novel item from a familiar one. Some studies suggest that systemic administration of angiotensin-(1-7) (Ang-(1-7)) attenuates CHF-induced spatial memory and object recognition impairment. Finally, Mas, the receptor for Ang-(1-7), is known to be expressed in the hippocampus and cortex. Thus, it is theorized that Ang-(1-7) activates Mas in the dorsal hippocampus and perirhinal cortex to decrease CHF induced cognitive impairment.

There are no studies, to date, examining the role and cell lar mechanisms of Ang-(1-7)Mas receptor axis in cognition and memory and its potential role as a cognitive protective agent in CHF and cardiovascular disease (CVD). However, in some studies, different rat models validate that Ang-(1-7) protects the cortex against reactive oxygen species (ROS)

mediated damage from cerebral ischemia. Again, this strongly implicates that the neuroprotective ability of Ang-(1-7) against CHF-induced cognitive impairment is mediated by central activation of the Ang-(1-7)/Mas signaling axis. Therefore, there is a need to enhance efficacy of action and, more importantly, penetration of the blood-brain barrier (BBB) of Ang-(1-7). Improved penetration of the blood-brain barrier will also facilitate cerebral entry of an Ang-(1-7) derivative, and, consequently, Mas activation, or intrinsic-efficacy. This glycosylation approach of the present invention may be promising for delivering Ang-(1-7) drugs to the Mas receptor for the treatment of spatial memory and object recognition impairment. Moreover, glycosylation promotes stability to peptidases, thereby increasing the half-life of the Ang-(1-7) derivatives in vivo.

The BBB prevents entry into the brain of many drugs from the blood. Thus, the presence of the BBB can make the development of new treatments of brain diseases (or new radiopharmaceuticals for neuroimaging of brain) difficult. Glycosylation of peptide chains can improve penetration of the BBB to facilitate cerebral entry of the glycopeptides derivative and consequently, activation of the target receptor, or intrinsic-efficacy. The present invention features glycosylated peptides have enhanced ability to cross the blood brain barrier (BBB) and/or enhanced half-lives. These glycosylated peptides may be used as drugs.

The present invention further features glycosylated peptides having a pseudoproline residue, with glycosylation at or near the C-terminus. A hydrogen bond is formed within an O-linked glycopeptide that has drug-like properties. The formation of a hydrogen bond produces a transient 5-membered ring that may be regarded as a "pseudoproline." Although "pseudo-prolines" have been referred to previously, those "pseudo-prolines" are formed via covalent bonds, and require chemical synthesis, whereas the pseudo-prolines describe herein form spontaneously in the peptide or protein chain upon attachment of the glycoside moiety.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features a peptide chain modified by the addition of glycosides to specific residues. According to an embodiment of the present invention, saccharides, such as a mono-, di-, tri- or poly-saccharide, can allow for pseudoproline bond interactions/formation in biologically active peptide chain. The native peptide remains generally intact with similar or better receptor binding. In a preferred embodiment, glycosylation modifies the amphipathicity of the glycopeptides, and not just the hydrophilic or hydrophobic nature alone. This greatly influences interaction with biological membranes, such as increasing their ability to cross membrane barriers like the blood-brain barrier.

According to an embodiment of the present invention, glycosides may be added to the aqueous face of the native peptide at sites on the aqueous surface and not the lipophilic surface. As a result, inherent binding of the glycopeptide to the native receptor is minimally affected; therefore, the glycosylated peptide derivatives can maintain receptor binding similar to that of the native peptide.

In some embodiments, the inherent amphipathicity of the folded glycopeptides and the "biousian approach" can facilitate delivery of the modified glycopeptides across the BBB. The BBB transport can occur via an absorptive endocytosis process on the blood side of the endothelium of the brain capillaries, followed by exocytosis on the brain side, leading to overall transcytosis. For this process to be efficient, the peptide must bind to the membrane for some period of time, and must also be able to exist in the aqueous state for some period of time (biousian nature). Effective drug delivery and BBB transport requires a biousian glycopeptide that essentially has two states: (1) a state defined by one or more membrane-bound conformations that permit or promote endocytosis; and (2) a state defined by a water-soluble, or random coil state that permits "membrane hopping". The degree of glycosylation does not have a large effect on the structure of the individual microstates. Thus, altering the degree of glycosylation allows for the modulation of aqueous versus membrane-bound state population densities.

In some embodiments, an alanine scan may be used to validate the surface of the native peptide, allowing for SAR optimization. According to some embodiments, the degree of glycosylation (unglycosylated Ser, glucosylated Ser, or lactosylated Ser) for optimal BBB transport may be determined using the best binding compounds using the in vivo mouse model. For example, in addition to lactose, the more robust cellobiose is examined using the best binding compounds. In some preferred embodiments, the results from the alanine scan may identify the residues that demonstrate increased interaction of the glycopeptides with the receptor (e.g. "hot spots"), and with a glycosylation state resulting in the penetration of the BBB. In some embodiments, non-peptidic D-amino acids and N-methylated amino acids, as well as un-natural amino acids may be substituted at one or two of the "hottest spots" to optimize binding. Therefore, a drug can be designed that exploits the glycopeptide lead structure(s) to produce a bona fide pharmaceutical entity.

Paradoxically, the present invention provides a method of surprisingly enhancing a peptide's ability to cross blood brain barrier (BBB) as well as surprisingly enhancing a peptide's half-life by substituting an amino acid in the C-terminal domain with a different amino acid adapted to be glycosylated (the different amino acid being the amino acid that is glycosylated with the glycan). Thus, adding a water-soluble group (e.g. a monosaccharide or disaccharide) promotes passage across a hydrophobic barrier. In some embodiments, the different amino acid is selected from the group consisting of: serine, threonine, cysteine, tyrosine, hydroxylysine, hydroxyproline, asparagine, arginine, or tryptophan, or derivatives thereof. A hydrogen bond is formed within an O-linked or S-linked glycopeptide that has drug-like properties. In other embodiments, the formation of a hydrogen bond produces a transient 5-membered ring that may be regarded as a "pseudoproline" and it enhances the peptide's half-life. Notably, these 0-linked or S-linked glycopeptides not only retained their agonist activity on PC12 cell cultures and in the quantitative CHO cell assay, but also showed greatly extended lifetimes in mouse serum, and provided evidence via microdialysis studies that the glycopeptides can cross the blood brain barrier in mice. Without wishing to limit the invention to any theory or mechanism, it is believed that the technical feature of the present invention advantageously beneficial in the treatment of migraine, and could also improve CNS drug delivery. None of the presently known prior references or work has the unique inventive technical feature of the present invention.

BRIEF DESCRIPTION OF THE DRAWINGS

This patent application contains at least one drawing executed in color. Copies of this patent or patent application publication with color drawing(s) will be provided by the Office upon request and payment of the necessary fee.

The features and advantages of the present invention will become apparent from a consideration of the following detailed description presented in connection with the accompanying drawings in which:

As shown in FIG. 3A, glycosylation of Ang1-7 produces a highly amphipathic folded structure that was characterized in silico using published NMR data as a starting point for the final calculated structure. A Solvent Accessible Surface Area was constructed using the MOE® software package and the AMBER-99 force field, and colorized red and blue to illustrate the resulting amphipathicity of the folded structure. FIG. 3B shows unfolded coil structures engaging in biousian behavior (reversible adsorption/desorption) in order to undergo transcytosis at the endothelial layer to traverse the BBB (1). Membrane hopping (2) is anticipated to lead to an efficient 2D membrane "search" for Mas receptors within the brain leading to binding (3) and receptor activation (4).

FIG. 7A: $PACAP_1$-2 and its glycosylated analogues degraded over 30 min in mouse serum at 37° C., as revealed by "shotgun" FI-$MS^n$ analysis. Data were fitted using a single exponential decay model ($R^2$>0.71, in all cases). FIG. 7B: Serine glucoside ($PACAP_{1-27\text{-}S\text{-}G}$, Glc) showed a significant increase in mouse serum $t_{1/2}$ in vitro compared to the native peptide $PACAP_{1-27}$ and the corresponding lactoside ($PACAP_{1-27\text{-}S\text{-}L}$, Lac) when compared using a 1-way analysis of variance (F2=12.91, p=0.0067, Tukey's multiple comparison Native vs Glc, q=5.760 p<0.05, Lac vs Glc, q=6.602 p<0.5). FIG. 7C: CLC-$MS^3$ allowed for rapid separation and simultaneous quantification of Native, Glc, and Lac PACAP derivatives. The $MS^2$ fragmentation pattern ($MS^2$ spectrum) for native PACAP, and the fragmentation patterns ($MS^3$ spectra) of Glc and Lac are shown. Interestingly, all resulted in the same primary fragment ion at 755 m/z. The specific ion transitions observed: $PACAP_{1-27}$ Native 630→755, $PACAP_{1-27\text{-}S\text{-}G}$, Glc 657→625→755→$PACAP_{1-27\text{-}S\text{-}L}$ Lac 690→625→755.

FIG. 9A: Variable concentration mode antagonist experiments. Concentration curves of $PACAP_{6-38}$, $PACAP_{6-27}$, and $PACAP_{6-27}$ derivatives were added to the cells for 2 minutes, followed by 5 nM of $PACAP_{1-27}$. The max-min response was determined, and normalized to the stimulation caused by 5 nM $PACAP_{1-27}$ (100%) and vehicle (0%). 3 variable non-linear curve fit (Prism), N=3-4 independent experiments, mean±SEM reported. Only $PACAP_{6-38}$ shows antagonism, but it is low potency. FIG. 9B: Fixed concentration mode experiments with $PACAP_{6-38}$. Fixed concentrations of $PACAP_{6-38}$ added to cells for 2 minutes, followed by concentration curves of $PACAP_{1-27}$. The max-min response was determined, and normalized to the max response of the $PACAP_{1-27}$ curve without antagonist present (100%) and vehicle (0%). Gaddum/Schild $EC_{50}$ Shift model (Prism), N=3 independent experiments. $PACAP_{6-38}$ shifts the curve only at the highest concentration (1 μM). FIG. 9C: Fixed concentration mode experiments with $PACAP_{6-27}$, performed as in B. N=3 independent experiments. $PACAP_{6-27}$ showed no detectable shifts in the agonist curves.

DESCRIPTION OF PREFERRED EMBODIMENTS

Figure 1:
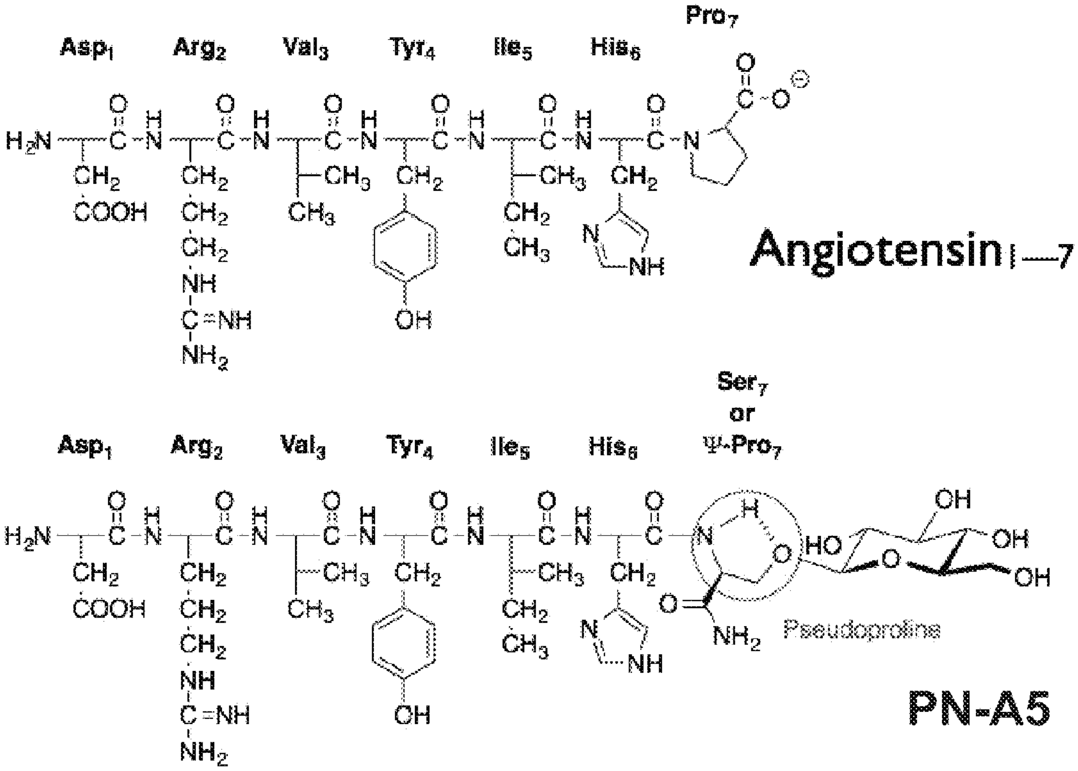
FIG. 1 shows a non-limiting example of a pseudoproline in an Angiotensin-(1-7) drug.
Figure 2:
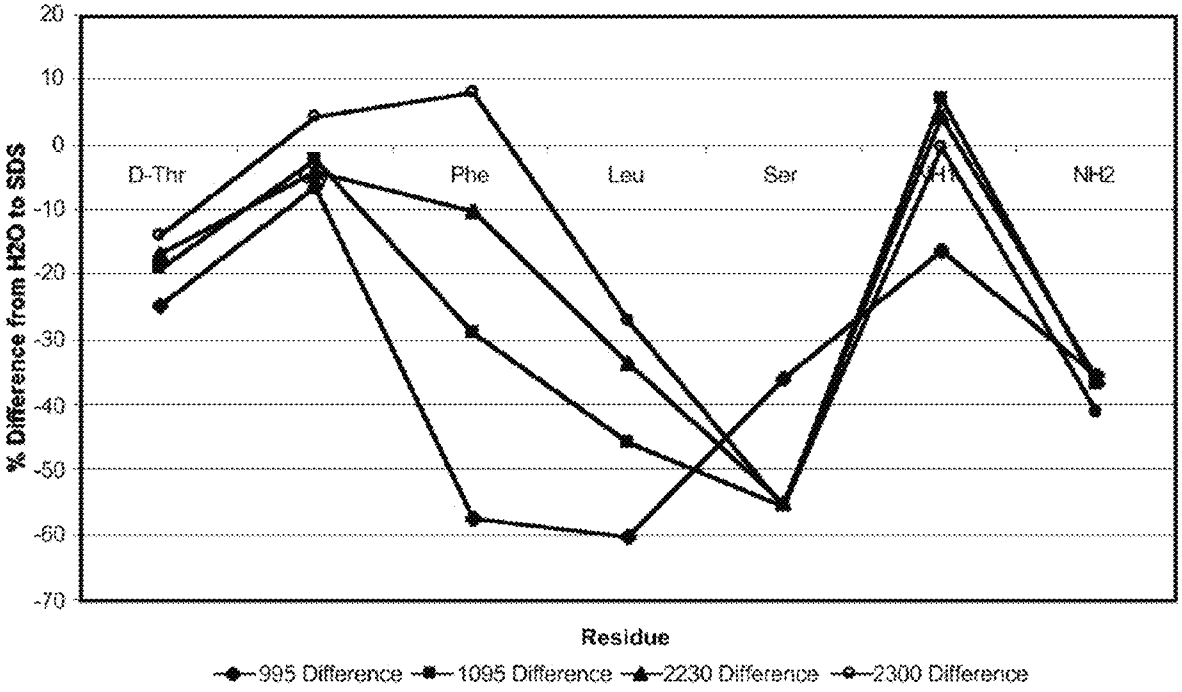
FIG. 2 is a graph of showing differences in H–H exchange rates determined by temperature-dependent 1H-NMR studies.
Figure 3A:
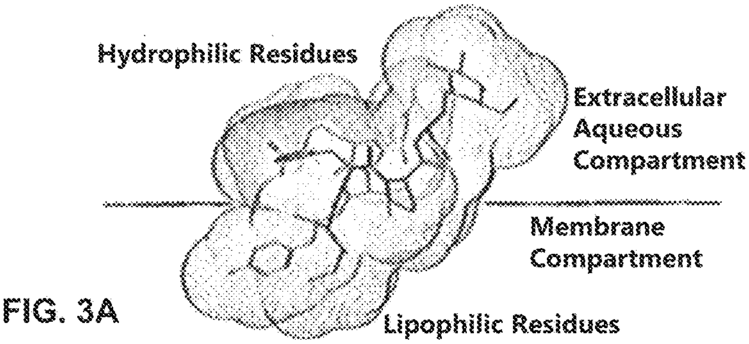
FIGS. 3A-3B shows an exemplary schematic of membrane Hopping and BBB Transport.
Figure 3B:
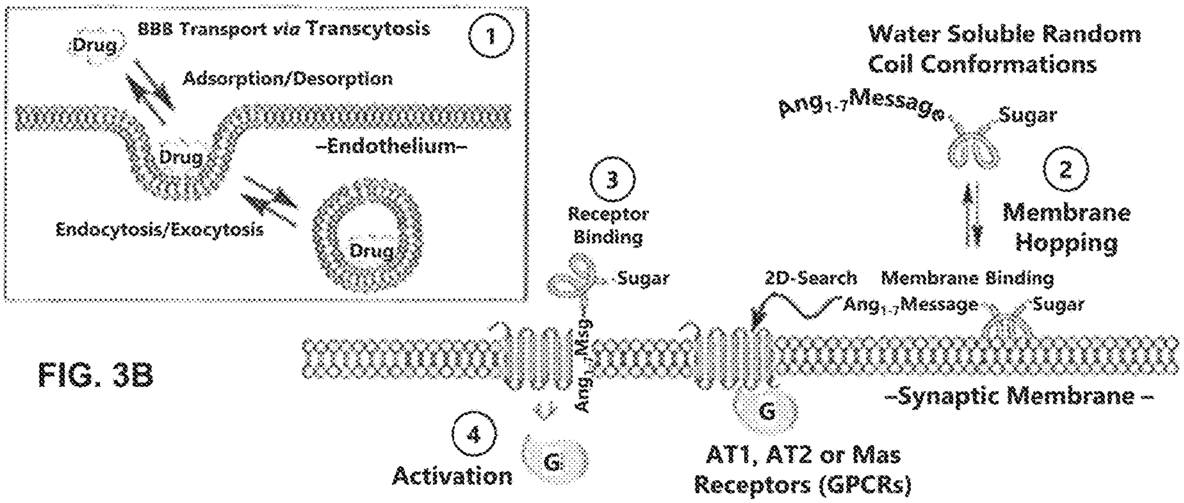
Figure 4:
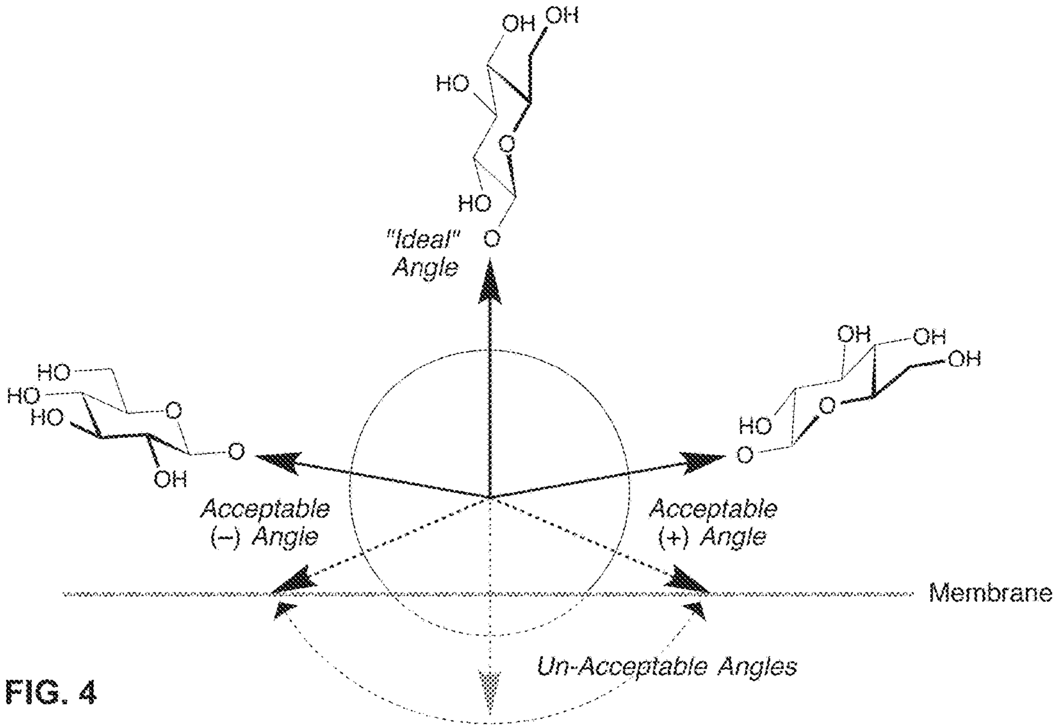
FIG. 4 shows how the angle of the glycoside moiety can be altered by the presence of the pseudoproline structure. The orientation of the glycoside moiety with respect to the peptide ligand and the membrane is ideally near 90°, although other lesser angles may be acceptable. Some angles are clearly unacceptable, and will interfere with membrane binding and subsequent receptor binding.
Figure 5:
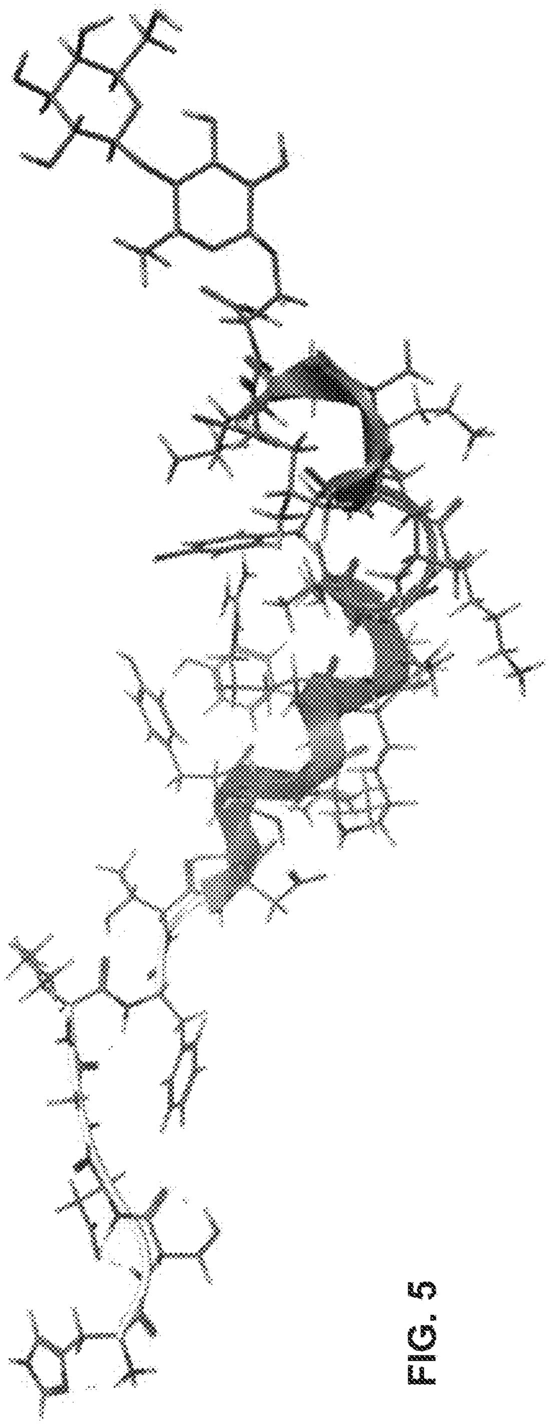
FIG. 5 shows Lactoside PACAP1-26-S-L, a molecular dynamics representation (MOE®) of PACAP1-27 that has been modified by replacing the terminal Leucine 27 amide with a Serine lactoside amide (Ser-O-β-D-Glc-β-D-Gal). The calculations suggest that the PACAP glycosides can adopt a largely helical conformation.

As used herein, the term "pseudoproline" is defined as a proline-mimicking residue. The pseudoproline comprises a transient 5-membered ring having a secondary amine.

As used herein, the term "glycoside" is defined a molecule formed by a carbohydrate or a saccharide bound to another reactive functional group via a glycosidic bond, which is a covalent bond formed between the hemiacetal group of the carbohydrate and the reactive functional group, such as the hydroxyl group, of another compound.

As used herein, the term "serine" encompasses serine in either its L- or D-configuration, as well as racemate or in various mixtures of its isomers or extended alkyl derivatives. As used herein, the term "threonine" encompasses threonine in either its L- or D-configuration, as well as racemate or in various mixtures of its isomers or extended alkyl derivatives. As used herein, the term "cysteine" encompasses cysteine in either its L- or D-configuration, as well as racemate or in various mixtures of its isomers or extended alkyl derivatives.

Glycopeptides with Pseudoproline

Referring now to FIG. 1-4, the present invention features a glycopeptide having at least one pseudoproline residue. The glycopeptide may be according to formula 1:

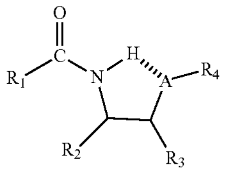

(1)

In some embodiments, A is an anomeric oxygen or a sulfur, $R_1$ is a first peptide chain, $R_2$ is a second peptide chain or —(C═O)$NH_2$, $R_3$ is a hydrogen or methyl, and $R_4$ is a glycoside moiety. Surprisingly, a pseudoproline residue is formed by hydrogen bonding of an amino functionality to the A being glycosidically bonded to the glycoside moiety. In some preferred embodiments, the glycopeptide has an increased ability to cross a blood brain barrier (BBB) as compared to a version of the glycopeptide lacking the glycosylation.

In some embodiments, the glycoside moiety can be a saccharide, such as a mono-, di-, tri- or poly-saccharide. Non-limiting examples of which include glucose, maltose, lactose, cellobiose, or any other saccharide as known to one of ordinary skill in the art. Moreover, the glycoside moiety may further include a and R forms of the saccharides. In other embodiments, the side peptide chain can be an enkephalin, an endorphin, a dynorphin, a vasoactive intestinal peptide (VIP), a pituitary adenylate cyclase-activating polypeptide (PACAP), an endogenous neuropeptide, a secretin family peptide, an angiotensin-(1-7) peptide and derivatives thereof, or any other peptide. For example, the glycopeptide may be a hormone, an agonist, or an antagonist that can bind to a target receptor.

Another embodiment of the present invention may feature a method for synthesizing a glycopeptide having at least one pseudoproline residue. In one embodiment, the glycopeptide may be according to formula 1:

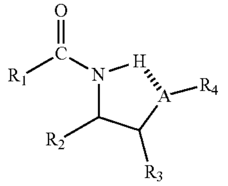

(1)

wherein A is an anomeric oxygen or a sulfur, $R_1$ is a first peptide chain, $R_2$ is a second peptide chain or —(C═O)$NH_2$, $R_3$ is a hydrogen or methyl, and $R_4$ is a glycoside moiety.

In some embodiments, the method may comprise synthesizing a glycosidic bond between a saccharide and a reactive functional group of a carrier amino acid to form a glycosylated amino acid, incorporating the glycosylated amino acid into an amino acid residue of $R_1$, and effecting ring closure by spontaneously forming a hydrogen bond between an amino group of the amino acid residue and the reactive functional group to form a pseudoproline, thereby forming the glycosylated peptide. In some embodiments, the carrier amino acid may comprise $R_2$, $R_3$, and the reactive functional group comprising A. For example, the reactive functional group may be an —OH or —SH. In other embodiments, the saccharide may comprise $R_4$.

In some embodiments, the carrier amino acid is serine, threonine, cysteine, or extended alkyl derivatives thereof. Examples of the carrier amino acid include, but are not limited to, Serine, D-Serine, Threonine, D-Threonine, allo-L-Threonine, allo-D-Threonine, Cysteine, D-Cysteine. In other embodiments, the first peptide chain or second peptide chain is an enkephalin, an endorphin, a dynorphin, a vasoactive intestinal peptide (VIP), a pituitary adenylate cyclase-activating polypeptide (PACAP), an endogenous neuropeptide, a secretin family peptide, an angiotensin-(1-7) peptide and derivatives thereof, or any other peptide. In further embodiments, the saccharide may be a mono-, di-, tri- or poly-saccharide. Non-limiting examples of which include glucose, maltose, lactose, cellobiose, or any other saccharide as known to one of ordinary skill in the art. Moreover, the glycoside moiety may further include a and R forms of the saccharides.

Embodiments of the glycopeptides described herein can have diverse biological functions. For example, the glycopeptide may be used for binding to a target receptor or for drug delivery. In some embodiments, the glycopeptide is amphipathic such that the glycopeptides can be water-soluble or membrane-bound. As used herein, the term "amphipathic" encompasses a molecule that has charged or highly polarized atoms bonds in the polar head, which is hydrophilic, and non-polar atoms and bonds in the tail, which are hydrophobic. As an example, a molecule can have a negatively or positively charged group or another water-soluble moiety, such as a sugar, in the polar head, which is hydrophilic, and non-polar atoms and bonds in the tail, which are hydrophobic. In one embodiment, the glycopeptide is folded along the side peptide chain such that charged groups of the glycopeptide are disposed on one end of the glycopeptide. In another embodiment, the glycopeptide is helical such that one surface of the helical glycopeptide has hydrophilic amino acids and the opposite face has hydrophobic (or lipophilic) amino acids. Preferably, the glycoside moiety, or saccharide, can effectuate crossing of the glycopeptide by adsorption and desorption from a biological membrane.

In some embodiments, the glycopeptides described herein may have various lengths. For example, in some embodiments, the glycopeptide is at least 5 amino acids in length. In other embodiments, the glycopeptide is at least 7 amino acids in length, at least 10 amino acids in length, at least 20 amino acids in length, or greater that 20 amino acids in length. In still further embodiments, the glycopeptide is not limited to the aforementioned lengths.

Glycosylated Peptides

Referring now to FIG. 5-10, the present invention features glycosylated peptides with glycosylation at or near the C-terminus. The glycosylated peptides have enhanced ability to cross the blood brain barrier (BBB) and/or enhanced half-lives. These glycosylated peptides may be used as drugs. For example, Pituitary Adenylate Cyclase Activating Peptide (PACAP) is a neuronal survival factor that acts as an agonist at the receptors $PAC_1$, $VPAC_1$, and/or $VPAC_2$. A PACAP peptide with a C-terminal glycosylation, e.g., in lieu of the terminal leucine, functions as a $PAC_1$ agonist with enhanced ability to cross the blood brain barrier and with enhanced half-life (without affecting receptor activation) (see Example 1). PACAP, as well as Vasoactive Intestinal Peptide (VIP) are closely related peptides from the Secretin Family, and are also survival factors that may be glycosylated in a similar fashion. The present invention also features PACAP and VIP antagonists.

As previously discussed, the present invention features glycosylated peptides, wherein at least one amino acid is glycosylated with a glycan. The peptides may be of various lengths. For example, in some embodiments, the peptide is at least 4 amino acids in length; or at least 5 amino acids in length; or at least 8 amino acids in length; or at least 10 amino acids in length; or at least 15 amino acids in length.

In some embodiments, the peptide is at least 20 amino acids in length; or at least 30 amino acids in length; or at least 40 amino acids in length; or at least 50 amino acids in length, or at least 60 amino acids in length. In other embodiments, the peptide is from 15 to 100 amino acids in length; or from 25 to 100 amino acids in length; or from 25 to 150 amino acids in length; or from 50 to 100 amino acids in length; or from 50 to 150 amino acids in length. The present invention is not limited to the aforementioned lengths.

In some embodiments, two or more amino acids are glycosylated with a glycan. In some embodiments, three or more amino acids are glycosylated with a glycan.

The C-terminal domain of the peptide may be defined by a group of amino acids at the C-terminus of the peptide. The C-terminal domain (e.g., the number of amino acids at the C-terminus of the peptide) may vary depending on the peptide. For example, in some embodiments, the C-terminal domain comprises the last amino acid at the C-terminus of the peptide. In some embodiments, the C-terminal domain comprises the last 2 amino acids at the C-terminus of the peptide. In some embodiments, the C-terminal domain comprises the last 3 amino acids at the C-terminus of the peptide. In some embodiments, the C-terminal domain comprises the last 4 amino acids at the C-terminus of the peptide. In some embodiments, the C-terminal domain comprises the last 5 amino acids at the C-terminus of the peptide. In some embodiments, the C-terminal domain comprises the last 6 amino acids at the C-terminus of the peptide. In some embodiments, the C-terminal domain comprises the last 7 amino acids at the C-terminus of the peptide. In some embodiments, the C-terminal domain comprises the last 8 amino acids at the C-terminus of the peptide. In some embodiments, the C-terminal domain comprises the last 9 amino acids at the C-terminus of the peptide. In some embodiments, the C-terminal domain comprises the last 10 amino acids at the C-terminus of the peptide. In some embodiments, the C-terminal domain comprises the last 15 amino acids at the C-terminus of the peptide. The C-terminal domain is not limited to the aforementioned number of amino acids at the C-terminus; in some embodiments, the C-terminal domain comprises the last 11, 12, 13, 14, 16, 17, 18, 19, 20, 21, 22, 23, 24, 25, etc. amino acids at the C-terminus of the peptide.

Glycosylation processes and glycans are well known to one of ordinary skill in the art. In some embodiments, the glycan is branched. In some embodiments, the glycan is unbranched. In some embodiments, the glycan is an N-linked glycan. In some embodiments, the glycan is an O-linked glycan. In some embodiments, the glycan is a C-linked glycan. In some embodiments, the glycan is an S-linked glycan. In some embodiments, the glycan is a phospho-serine glycan.

In some embodiments, the glycan comprises glucose. In some embodiments, the glycan comprises lactose. In some embodiments, the glycan comprises maltose. In some embodiments, the glycan comprises cellobiose. In some embodiments, the glycan comprises melibiose. In some embodiments, the glycan comprises linear or branched trisaccharides of glucose. In some embodiments, the glycan comprises N-acetylglucosamine. In some embodiments, the glycan comprises galactose. In some embodiments, the glycan comprises N-acetylgalactosamine. In some embodiments, the glycan comprises galactosamine. In some embodiments, the glycan comprises glucosamine. In some embodiments, the glycan comprises mannose. In some embodiments, the glycan comprises N-acetylmannosamine. In some embodiments, the glycan comprises mannosamine. In some embodiments, the glycan comprises xylose.

In some embodiments, the glycan comprises N-acetylneuraminic acid. In some embodiments, the glycan comprises N-glycolylneuraminic acid. In some embodiments, the glycan comprises 2-keto-3-deoxynononic acid. In some embodiments, the glycan comprises fucose. In some embodiments, the glycan comprises iduronic acid. In some embodiments, the glycan comprises glucuronic acid. In some embodiments, the glycan comprises cellobiose. In some embodiments, the glycan comprises melibiose. In some embodiments, the glycan comprises rhamnose. The present invention is not limited to the aforementioned glycans. For example, the glycan of the present invention may be selected from all mono-, di-, tri- and poly-saccharides.

In some embodiments, the glycosylated peptide has an increased ability to cross a blood brain barrier (BBB) as compared to a version of the glycosylated peptide lacking the glycosylation. In some embodiments, the glycosylated peptide has an increased half-life as compared to a version of the glycosylated peptide lacking the glycosylation.

In some embodiments, an amino acid in the C-terminal domain (of the peptide) is substituted with a different amino acid, the different amino acid is adapted to be glycosylated, the different amino acid being the amino acid glycosylated with the glycan. In some embodiments, a different amino acid (e.g., a glycosylated amino acid) is appended to the C-terminus of a peptide. The different amino acid may be selected from the group consisting of: serine, threonine, cysteine, tyrosine, hydroxylysine, hydroxyproline, asparagine, arginine, or tryptophan, and any reasonable alkyl derivative thereof.

Referring to Example 1 below, in some embodiments, the glycosylated peptide is a PAC$_1$ agonist. The PAC$_1$ agonist may comprise a PACAP peptide, e.g., a PACAP peptide wherein an amino acid in the C-terminal domain is glycosylated with a glycan. In some embodiments, the terminal leucine residue is substituted with a serine (the serine being the amino acid glycosylated with the glycan). As such, the present invention features a PAC$_1$ agonist comprising a PACAP peptide, wherein an amino acid in a C-terminal domain of the PACAP peptide is glycosylated with a glycan. Again referring to Example 1, in some embodiments, the glycosylated peptide (e.g., the PAC$_1$ agonist) is selected from the group consisting of:

```
(SEQ ID NO: 1)
HSDGIFTDSY10SRYRKQMAVK20KYLAAVL;

(SEQ ID NO: 2)
HSDGIFTDSY10SRYRKQMAVK20KYLAAVS-O-β-D-Glc;

(SEQ ID NO: 3)
FTDSY10SRYRKQMAVK20KYLAAVL;

(SEQ ID NO: 4)
FTDSY10SRYRKQMAVK20KYLAAVLGKR30YKQRVKNY;

(SEQ ID NO: 5)
FTDSY10SRYRKQMAVK20KYLAAVS-O-β-D-Glc;

(SEQ ID NO: 6)
FTDSY10SRYRKQMAVK20KYLAAVS-O-β-D-Glc-β-D-Gal;

(SEQ ID NO: 7)
FTDSY10SRYRRQLAVR20RYLAAVL;

(SEQ ID NO: 8)
FTDSY10SRYRRQLAVR20RYLAAVS-O-β-D-Glc;
and

(SEQ ID NO: 9)
FTDSY10SRYRRQLAVR20RYLAAVS-O-β-D-Glc-β-D-Gal;
```

In some embodiments, the PAC$_1$ agonist (e.g., the PAC$_1$ agonist comprising a PACAP peptide wherein an amino acid in a C-terminal domain of the PACAP peptide is glycosylated with a glycan) has an increased ability to cross a blood brain barrier (BBB) as compared to a version of the glycosylated peptide lacking the glycosylation. In some embodiments, the PAC$_1$ agonist (e.g., the PAC$_1$ agonist comprising a PACAP peptide wherein an amino acid in a C-terminal domain of the PACAP peptide is glycosylated with a glycan) has an increased half-life as compared to a version of the glycosylated peptide lacking the glycosylation.

Another embodiment of the present invention may feature a composition of a glycopeptide having at least one pseudoproline residue. The composition may comprise a structure as follows:

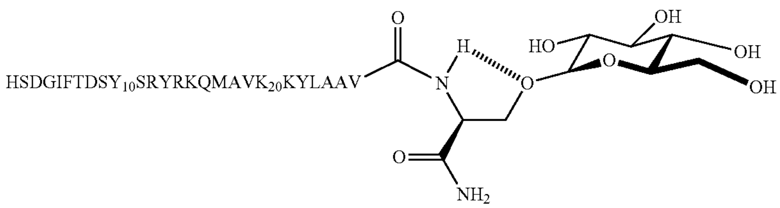

wherein HSDGIFTDSY$_{10}$SRYRKQMAVK$_{20}$KYLAAV=pituitary adenylate cyclase-activating peptide (PACAP$_{1-26}$) (SEQ ID NO: 10).

In another embodiment, the present invention may feature a composition of a glycopeptide having at least one pseudoproline residue. The composition may comprise a structure as follows:

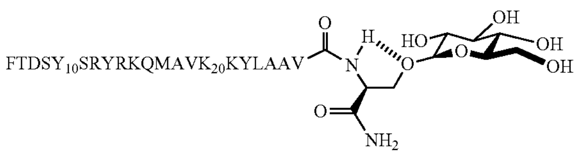

wherein FTDSY$_{10}$SRYRKQMAVK$_{20}$KYLAAV=pituitary adenylate cyclase-activating peptide (PACAP$_{6-26}$) (SEQ ID NO: 11).

A further embodiment of the present invention may feature a composition of a glycopeptide having at least one pseudoproline residue. The composition may comprise a structure as follows:

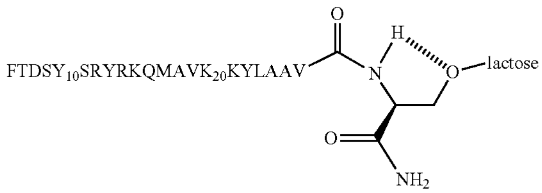

wherein FTDSY$_{10}$SRYRKQMAVK$_{20}$KYLAAV=pituitary adenylate cyclase-activating peptide (PACAP$_{6-26}$) (SEQ ID NO: 11), and lactose=(-β-D-Glc-β-D-Gal).

In another embodiment, the present invention may feature a composition of a glycopeptide having at least one pseudoproline residue. The composition may comprise a structure as follows:

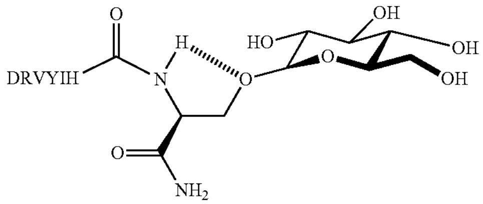

wherein DRVYIH=angiotensin peptide (Ang-(1-6)) (SEQ ID NO: 12).

A composition of a glycopeptide having at least one pseudoproline residue. The composition may comprise a structure as follows:

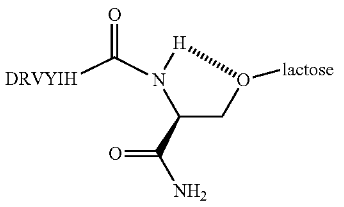

wherein DRVYIH=angiotensin peptide (Ang-(1-6)) (SEQ ID NO: 12), and lactose=(-β-D-Glc-β-D-Gal).

The present invention also features methods of use of said glycosylated peptides as well as various other methods involving said glycosylated peptides. For example, the present invention features a method of enhancing a peptide's ability to cross a blood brain barrier (BBB). The method may comprise introducing glycosylation to an amino acid in a C-terminal domain of the peptide (e.g., as described herein). The present invention also features a method of enhancing a peptide's half-life. In some embodiments, the method comprises introducing glycosylation to an amino acid in a C-terminal domain of the peptide. For example, in some embodiments, the method comprises forming the glycan-amino acid conjugate and including that conjugate in standard peptide synthesis conditions. In some embodiments, the carbohydrate is introduced synthetically.

In some embodiments, the method of enhancing the peptide's ability to cross the BBB and/or the method of enhancing a peptide's half-life further comprises substituting an amino acid in the C-terminal domain with a different amino acid adapted to be glycosylated (the different amino acid being the amino acid that is glycosylated with the glycan). As previously discussed, in some embodiments, the different amino acid is selected from the group consisting of: serine, threonine, cysteine, tyrosine, hydroxylysine, hydroxyproline, asparagine, arginine, or tryptophan, or derivatives thereof.

In some preferred embodiments, any of the glycopeptide or glycosylated peptides described herein can be cyclized either in solution or while still on a resin using amide bonds (O═C—N), disulfide bonds (S—S), or olefins (C═C, stapling).

Example 1

Example 1 describes the study of peptides and O-linked glycopeptides related to Pituitary Adenylate Cyclase Activating Peptide (PACAP) for their potential as agonist neuroprotective agents and antagonist anti-migraine agents. Briefly, activation of human $PAC_1$ receptors expressed in Chinese Hamster Ovary (CHO) cells was observed for $PACAP_{1-27}$, as well as its glucoside analogue ($PACAP_{1\text{-}27\text{-}S\text{-}G}$) with similar potency and efficacy. The glucoside ($PACAP_{1\text{-}27\text{-}S\text{-}G}$) showed enhanced stability in the presence of mouse serum, and its presence in mouse brain could be detected after i.p. administration by flow-injection tandem mass spectrometry ($MS^3$). Both the glucoside and the lactoside derivatives promoted differentiation of pheochromocytoma cells (PC12 cells) grown in culture, suggesting endogenous $PAC_1$ agonism. In addition glycosylated derivatives of $PACAP_{6-27}$ were tested as potential $PAC_1$ antagonists for the treatment of migraine. These compounds did not display antagonist activity, yet neither did the putative $PAC_1$ antagonists $PACAP_{6-27}$ and $PACAP^{6-38}$, suggesting that another target or mechanism may be involved. The present invention is not limited to the compounds, configurations, methods, and systems described in Example 1.

Methods

1. Peptide and Glycopeptide Synthesis

Unless otherwise noted, all solvents were obtained from EMD Chemicals (Gibbstown, N.J.), and used without further purification. Fmoc-protected amino acids Fmoc-Ala-OH, Fmoc-Lys(Boc)-OH, Fmoc-Leu-OH, Fmoc-Met-OH, Fmoc-Tyr(tBu)-OH, and condensing agent N,N'-diisopropylcarbodiimide (DIC) were acquired from Advanced ChemTech (Louisville, Ky., USA). Fmoc-Asp(tBu)-OH was acquired from Oxchem Corporation (Los Angeles, Calif., USA). Fmoc-Phe-OH, Fmoc-Gly-OH, Fmoc-Ile-OH, Fmoc-Gln(Trt)-OH, Fmoc-Ser(tBu)-OH, and Fmoc-Val-OH were acquired from Chem-Impex (Wood Dale, Ill., USA). Fmoc-His(Trt)-OH, Fmoc-Arg(Pbf)-OH, Fmoc-Thr(tBu)-OH, Fmoc-Nle-OH, and Hydroxybenzotriazole hydrate (HOBt-$H_2O$) were obtained from AAPPTec (Louisville, Ky., USA). 1,8-diazabicyclo[5.4.0]undec-7-ene (DBU) from TCI America (Portland, Oreg., USA), piperidine from Sigma-Aldrich (St. Louis, Mo., USA), piperizine from Alfa Aesar (Ward Hill, Mass., USA), 0-(7-Azabenzotriazol-1-yl)-N,N,N',N'-tetramethyluronium hexafluorophosphate (HATU) from Accela ChemBio Co., Ltd (Hong Kong, China), 2,4,6-trimethylpyridine (TMP) from Acros Organics (Geel, Belgium), and 1-Methyl-2-pyrrolidinone from Avantor (Center Valley, Pa., USA). $PACAP_{6-38}$ was obtained from commercial sources (Tocris, Bristol, UK).

Peptide and glycopeptide assembly was accomplished using a combination of manual and automated peptide methods. A general procedure follows: The C-terminal amino acids were loaded onto Fmoc-Rink resin (Advanced ChemTech, Louisville, Ky., USA) at 0.1 mmol/g resin loading in 25 mL fritted syringes. Initially, the resin was swelled using dimethylformamide (DMF, ~5 mL solvent per gram resin), agitating at RT for two minutes (×2). A solution of 2% DBU and 3% piperidine in DMF (v:v) was introduced and agitated for 5 minutes, refreshed, and agitated for an additional 10 minutes. The resin was washed with DMF (×5), and finally with N-methylpyrrolidine (NMP). In a separate vial, Fmoc-β-OGlc$(OAc)_4$-Ser-OH (0.12 mmol, 1.2 eq) was dissolved in 5 mL NMP, and HOBt-$H_2O$ (0.13 mmol, 1.3 eq) was added and allowed to mix for 5 minutes. Condensing agent DIC (0.26 mmol, 2.6 eq) was then added, and mixed for 5 minutes. This solution was added to the resin and agitated for 10 minutes. Next, the syringe was placed in a microwave (Emerson 900 W Microwave—MW9338SB) set to power level 1 and irradiated for 10 minutes, stopping to shake the syringe every 90 seconds. The syringe was then agitated at RT for an additional 30 minutes. The resin was washed with NMP (×1), DMF (×5), and $CH_2Cl_2$ (×5), and dried in vacuo overnight.

Peptides and glycopeptides also were assembled on a Prelude® Peptide Synthesizer (Protein Technologies, Inc., Tucson, Ariz., USA) using the reaction scheme that follows: Rink resin (100 mg) was placed into the fritted reaction vessels (RVs). Amino acids were dissolved in DMF at 250 mM concentration, HATU at 375 mM, and TMP at 3M. The following steps were performed for coupling: DMF Top Wash (1.5 mL, 2 min mix and drain; ×6), Deprotection (2% DBU/3% piperidine in DMF; 1.5 mL, 4 min mix and drain; 8 min mix and drain), DMF Top Wash (1.5 ml, 2 min mix and drain; ×5), Amino Acid Building Block (0.950 mL, 30 sec mix), Activator 1 (HATU, 0.650 mL, 30 sec mix), Base (TMP, 0.300 mL, 35 min mix and drain), DMF Top Wash (1.5 mL, 2 min mix and drain; ×2). After coupling aspartic acid D7, the deprotection solution was changed to 0.1 M $HOBt.H_2O$/5% piperazine in DMF to minimize aspartimide formation.

Cleavage of the peptides and glycopeptides from the resin was accomplished with a TFA "cocktail" of $F_3CCOOH$: $Et_3SiH$:$H_2O$:$CH_2Cl_2$:Ph-$OCH_3$ (by volume, 9:0.3:0.2:1: 0.05), agitating at RT for 2 hours. The resulting solutions were expelled into 15 mL centrifuge tubes, evaporated under argon, precipitated in ice-cold $Et_2O$, decanted, and rewashed with $Et_2O$, then dissolved in $H_2O$ and lyophilized to afford the crude material as fluffy white solids.

Purification of the crude glycopeptides was accomplished by Reversed Phase HPLC (RP-HPLC) with a preparative RP (C-18) Phenomenex (250×22 mm) column using a $CH_3CN$—$H_2O$ gradient solvent system containing 0.1% $F_3CCOOH$. Homogeneity of the purified glycopeptides was confirmed by analytical RP-HPLC and high resolution mass spectrometry.

2. Stability Studies in Mouse Serum by $MS^n$

Flow-injection tandem mass spectrometry (FI-$MS^n$) was used to observe the degradation of the peptides and glycopeptides with a Thermo LCQ with electrospray ionization (ESI). The technique involved injection of a sample bolus of material in mouse serum via a six port valve with fluid flow delivered via a syringe pump, and subsequent electrospray ionization (ESI) followed by mass spectral analysis. Samples were diluted to a concentration of ~5 μM of each PACAP analogue, and were incubated at 37° C. for times varying from 1 to 60 minutes. After samples had been incubated for the prescribed amount of time they were prepared for mass spectrometry analysis by withdrawing 10 microliters of solution and spiking with 1 microliter of a 10 μM solution of peptide internal standard (angiotensin II) in 50% acetic acid and subjecting them to a standard C18 zip tip desalting. These solutions, once eluted from the zip tip were diluted to 100 μL in 50:50 acetonitrile/water with 0.1% formic acid. Tandem mass spectrometry analysis ($MS^3$) was conducted to yield specific, quantitative signals proportional to the amount of PACAP analogue at each time point. This technique was also used with microdiasylate samples from a mouse after i.p. administration of PACAP1-27-S-G.

3. $PAC_1$ Cell Line and Cell Culture

A custom DNA clone of the human PAC1 gene with 3 hemagglutinin (HA) tags inserted 3' to the signal peptide sequence (to avoid proteolytic loss) was obtained from Genecopoeia (Rockville, Md.). The construct was electroporated into Chinese Hamster Ovary (CHO) cells, and selected for with 500 μg/mL of G418. The resulting population was screened for high expressing clones, and one such clone selected for further analysis. The clonal cell line ($PAC_1$-CHO) displayed high receptor expression by immunocytochemistry and Western blot, and showed selective activation of signaling in response to $PACAP_{1-27}$ (data not shown). This cell line was used for all molecular pharmacology experiments. The cells were maintained in DMEM/F12 with 10% heat-inactivated FBS, 1× penicillin/streptomycin, and 500 μg/mL G418, at 37° C. and 5% $CO_2$.

4. Fluorescent Imaging Plate Reader (FLIPR) Experiments

All molecular pharmacology experiments were carried out using a FLIPR Tetra from Molecular Devices (Sunnyvale, Calif.), set to image calcium flux using the manufacturer's recommended settings and protocols. The day before an experiment, the $PAC_1$-CHO cells were split into 384 well black walled, clear bottom microplates, 10,000 cells per well. The cells were recovered overnight in growth medium (as above). The next day, the growth medium was replaced with Calcium 6 dye (Molecular Devices) using the manufacturer recommended buffer with 2.5 mM probenecid. The cells were incubated for 2 hours in the culture incubator, and removed during the last 15 minutes to allow equilibration to room temperature. Compound as indicated below was added to the cells using a 384 tip block, with real time monitoring before, during, and 15 minutes after compound addition. The resulting calcium flux was recorded, and the maximum-minimum response over the entire observation time calculated and reported as the mean±SEM (4 wells per point).

For agonist mode experiments, compound was added in an 11 point concentration curve, with a vehicle control (buffer). The resulting response was normalized to the stimulation caused by $PACAP_{1-27}$ (100%) and vehicle (0%). The response was analyzed using a 3 variable non-linear curve fit, and the $EC_{50}$ (nM) and $E_{Max}$ (%) calculated and reported (Prism, GraphPad, La Jolla, Calif.).

For antagonist mode experiments, a concentration curve (variable concentration mode) or fixed amount (fixed concentration mode) of antagonist was added to the cells, and allowed to equilibrate for 2 minutes. Then, either a 5 nM fixed conentration (variable concentration mode) or an 11 point concentration curve (fixed concentration mode) of $PACAP_{1-27}$ was added to the cells, and the max-min response recorded as above. For variable concentration mode experiments, the data was normalized to the stimulation caused by 5 nM $PACAP_{1-27}$ (100%) and vehicle (0%), and analyzed with a 3 variable non-linear curve fit, with the $IC_{50}$ (nM) and $I_{Max}$ (%) calculated and reported (Prism). For the fixed concentration mode experiments, each curve was normalized to the maximum stimulation caused by $PACAP_{1-27}$ with no antagonist present (100%) and vehicle (0%). The resulting data was analyzed using a Gaddum/Schild $EC_{50}$ shift model, (Schild, 1957, Gaddum, 1957) designed to analyze competitive antagonism. The data output was the pA2 (nM) and the Schild Slope, a measure of how closely the experimental data fits the operational model of competitive antagonism (Prism). For all analyses, each independent experiment performed in quadruplicate is considered to be a sample size of 1. The pharmacology values are calculated separately from each experiment, then combined and reported as the mean±SEM for the entire set of experiments.

5. Effects on Differentiation of Cultured PC12 Cells

The PC12 cells were cultured in RPMI containing 5% heat inactivated fetal bovine serum and 10% horse serum in the presence of 100 units/mL penicillin and 100 microgram/mL streptomycin. The cells were plated on poly-D-Lysine coated 6-well tissue culture plates at a density of 150,000 cells per well in 2 mL media. After 48 hours at 37° C. in 5% $CO_2$ atmosphere, media exchange was performed and plates were dosed, using the peptide diluent (water) for the control samples. $PACAP_{1-27}$, $PACAP_{1-27-S-G}$, and $PACAP_{1-27-S-L}$ were used to screen for $PAC_1$ receptor activation. Four groups of cells were used; one control group (diluent treated) and three treatment groups, each treatment group was exposed to 100 nM concentrations of $PACAP_{1-27}$, $PACAP_{1-27-S-G}$, or $PACAP_{1-27-S-L}$. All groups were run in triplicate. Cell images of each treatment group were captured and compared to the control cells to screen for differentiation and cell body volume increases. Cells having neurite-like process outgrowth were noted and photographed. The neurite-like outgrowth was deemed positive if its length was at least two times the width of the cell body.

Results

1. Synthesis of PACAP Derivatives

PACAP derivatives and glycosides were synthesized on a small scale (~5 mg) using solid-phase methods previously described (Polt, et al., General Methods for α- or β-O-Ser/Thr Glycosides and Glycopeptides. Solid-Phase Synthesis of O-Glycosyl Cyclic Enkephalin Analogues. J. Am. Chem. Soc. 114, 10249-10258 (1992); Mitchell, et al., Solid-Phase Synthesis of O-Linked Glycopeptide Analogues of Enkephalin. J. Org. Chem. 66, 2327-2342 (2001)). For example, see FIG. 5 and Table 1 (below). Recent advances in the synthesis of Fmoc-protected glycosides of Serine and Threonine using "minimally competent" Lewis acid promoters allows for production of required glycosides in high yield and purity, which in turn provides either linear or cyclic variants of O-linked glycopeptides.

Table 1 shows peptides and glycopeptides in the present invention. The truncated peptides and glycopeptides are missing five N-terminal amino acids responsible for binding to the transmembrane portion of the GPCR receptors and were considered to be antagonists. For the glycosides, Leucine 27 has been replaced (underlined residues) by a Serine glycoside bearing glucose (-β-D-Glc) or lactose (-β-D-Glc-β-D-Gal). The final 3 alternate compounds have been modified by replacing methionine 17 with Leucine, and Lysines 15, 20 and 21 with Arginines to enhance stability in vivo, and were expected to be antagonists at $PAC_1$.

TABLE 1

| | Peptides | | |
|---|---|---|---|
| Glycopeptides | Amino Acid Sequence (C-Terminal Amides) | SEQ ID NO: | MW |
| PACAP1-27 | $HSDGIFTDSY_{10}SRYRKQMAVK_{20}KYLAAVL$ | 1 | 3,938 |
| PACAP1-27-S-G | $HSDGIFTDSY_{10}SRYRKQMAVK_{20}KYLAAVS$-O-β-D-Glc | 2 | 4,242 |
| PACAP6-27 | $FTDSY_{10}SRYRKQMAVK_{20}KYLAAVL$ | 3 | 3,316 |
| PACAP6-38 | $FTDSY_{10}SRYRKQMAVK_{20}KYLAAVLGKR_{30}YKQRVKNY$ | 4 | 4,534 |
| PACAP6-27-S-G | $FTDSY_{10}SRYRKQMAVK_{20}KYLAAVS$-O-β-D-Glc | 5 | 3,452 |
| PACAP6-27-S-L | $FTDSY_{10}SRYRKQMAVK_{20}KYLAAVS$-O-β-D-Glc-β-D-Gal | 6 | 3,614 |
| PACAP6-27-Alt | $FTDSY_{10}SRYRRQLAVR_{20}RYLAAVL$ | 7 | 3,382 |
| PACAP6-27-S-G-Alt | $FTDSY_{10}SRYRRQLAVR_{20}RYLAAVS$-O-β-D-Glc | 8 | 3,518 |
| PACAP6-27-S-L-Alt | $FTDSY_{10}SRYRRQLAVR_{20}RYLAAVS$-O-β-D-Glc-β-D-Gal | 9 | 3,681 |

2. Stability in Mouse Serum

Figure 6:
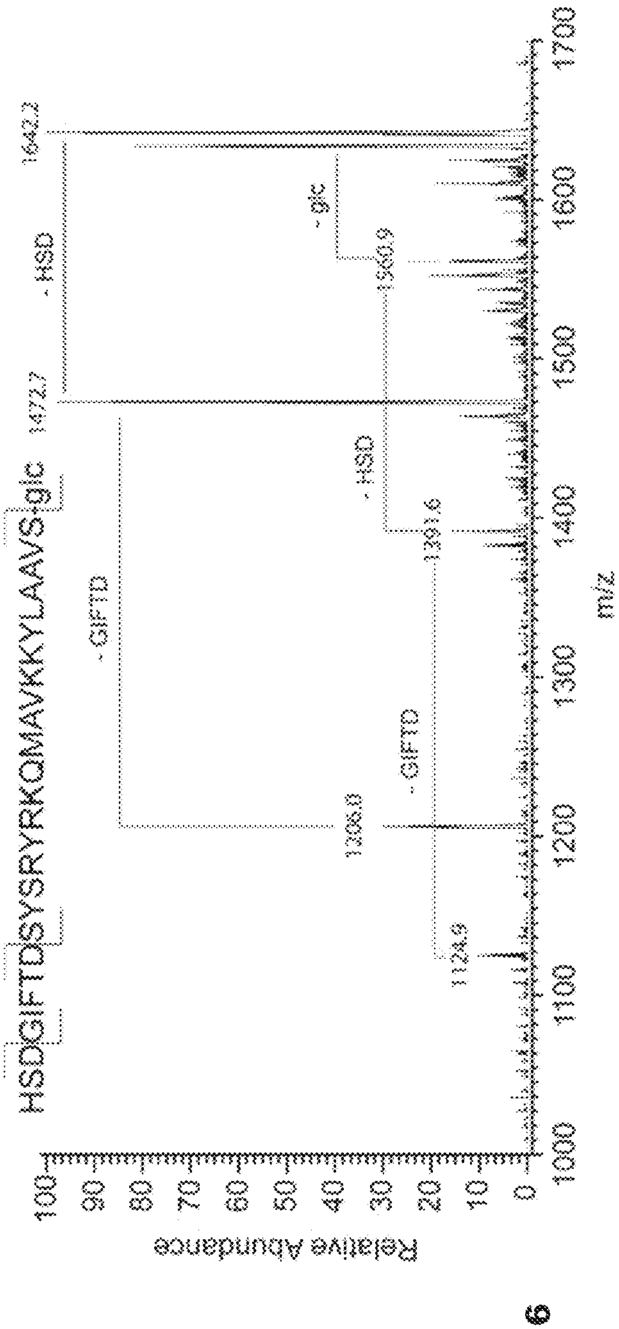
FIG. 6 shows MS Fragmentation of Glucoside $PACAP_{1-27\text{-}S\text{-}G}$. Collision induced fragmentation of the $2^+$ ion at 1642.7 m/z from mouse brain dialysate carried out using MS/MS. This spectrum shows a clear pattern from the N-terminus in which fragmentation occurs at the aspartic acid residues resulting $y^{2+}$ ions. The glycosylated $y_{19}{}^{2+}$ and $y_{24}{}^{2+}$ at 1206.0 and 1472.7 m/z respectively, are the predominant ions in the spectrum ($NH_3$ loss omitted for clarity). P-Glc cleavage gave 1560.9 m/z, matching the calculated mass for $PACAP_{1-27}$ with a C-terminal amide. Loss of the glucoside along with peptide backbone cleavage resulted in $y_{19}{}^{2+}$ and $y_{24}{}^{2+}$ ions at 1124.9 and m/z 1391.6.
Figure 7A:
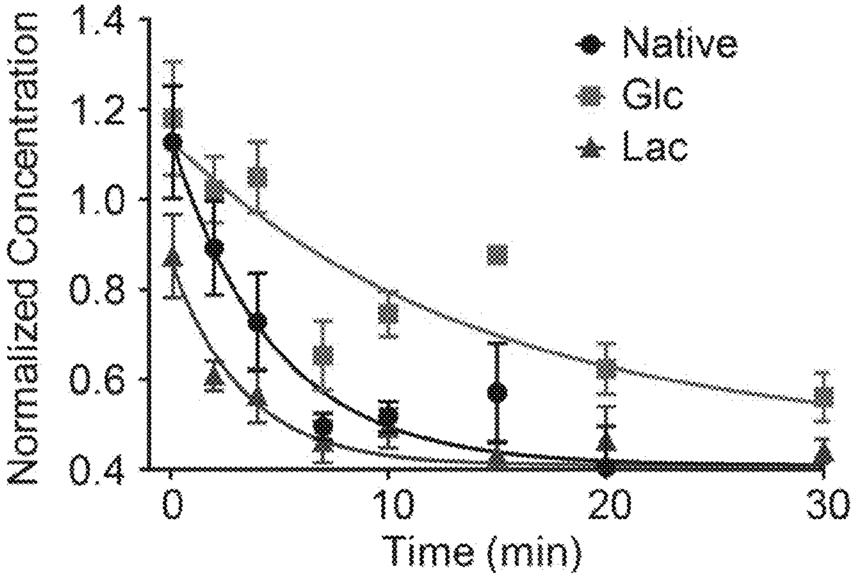
FIGS. 7A-7C show stability of $PACAP_{1-27}$, $PACAP_{1-26\text{-}S\text{-}G}$, and $PACAP_{1-27\_S\text{-}L}$.
Figure 7B:
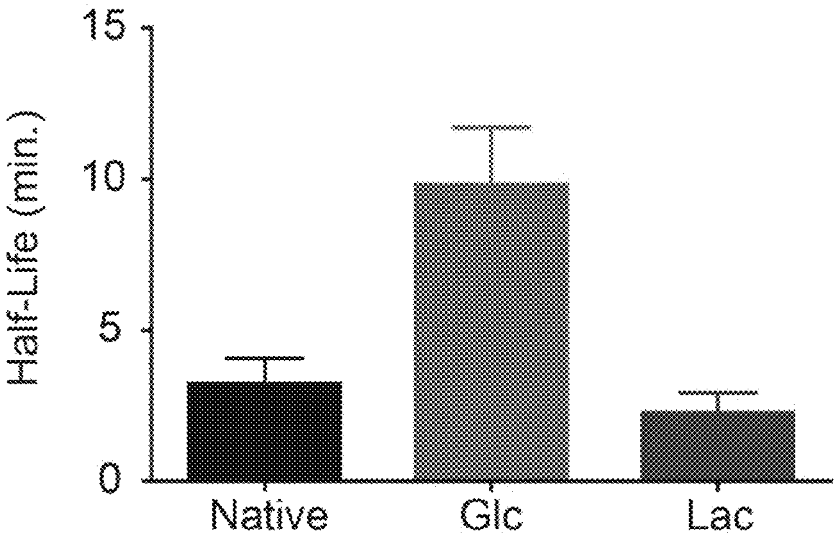
Figure 7C:
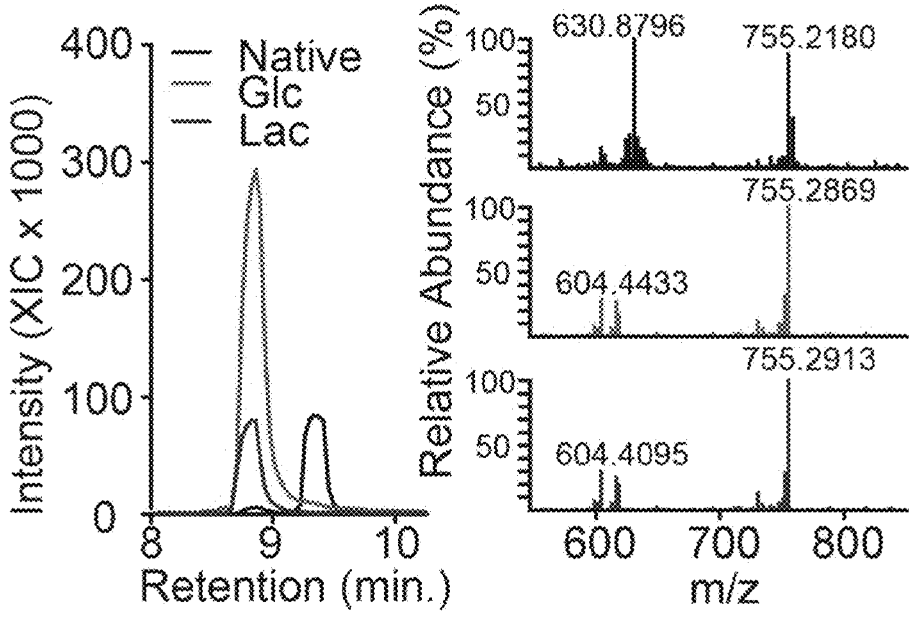
Figure 8:
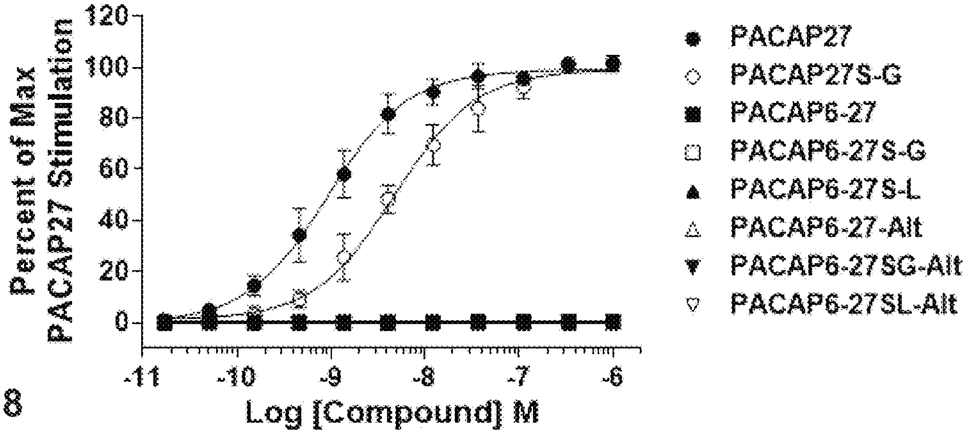
FIG. 8 shows agonist activity of PACAP derivatives at $PAC_1$. $PAC_1$-CHO calcium flux activation was measured using FLIPR in response to 11 point concentration curves of $PACAP_{1-27}$, the glucoside $PACAP_{1-27\text{-}S\text{-}G}$, and the truncated derivatives (putative antagonists) of $PACAP_{6-27}$. Response was measured over 10 minutes, the max-min calculated, and all data was normalized to the maximum response caused by $PACAP_{1-27}$ (100%) and vehicle (0%). The mean±SEM is shown, using the mean value from each independent experiment. N=3 independent experiments performed, 3 variable non-linear curve fit using Prism. Derived values reported in Table 2. $PACAP_{1-27}$ and $PACAP_{1-27\text{-}S\text{-}G}$ display potent, efficacious agonist activity.
Figure 9A:
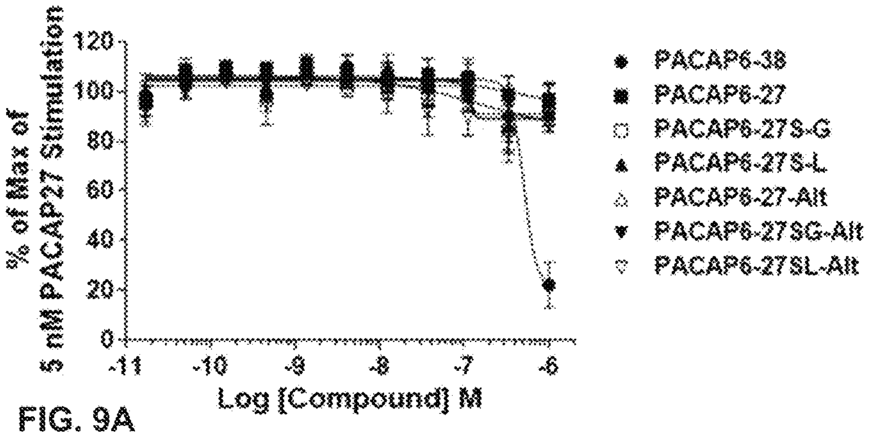
FIGS. 9A-9C show antagonist activity of PACAP derivatives at $PAC_1$. The ability of $PACAP_{6-27}$ derivatives to block $PACAP_{1-27}$ induced calcium flux was measured using FLIPR. Derived values are reported in Table 2.
Figure 9B:
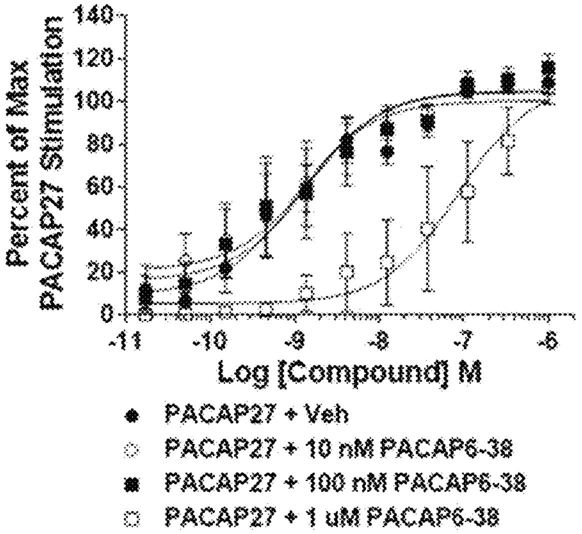
Figure 9C:
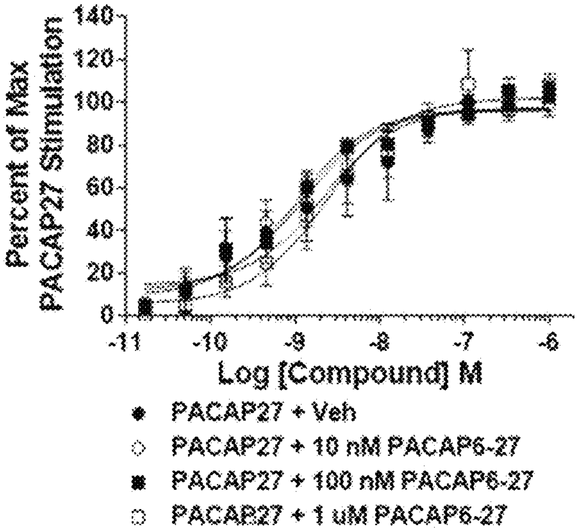
Figure 10:
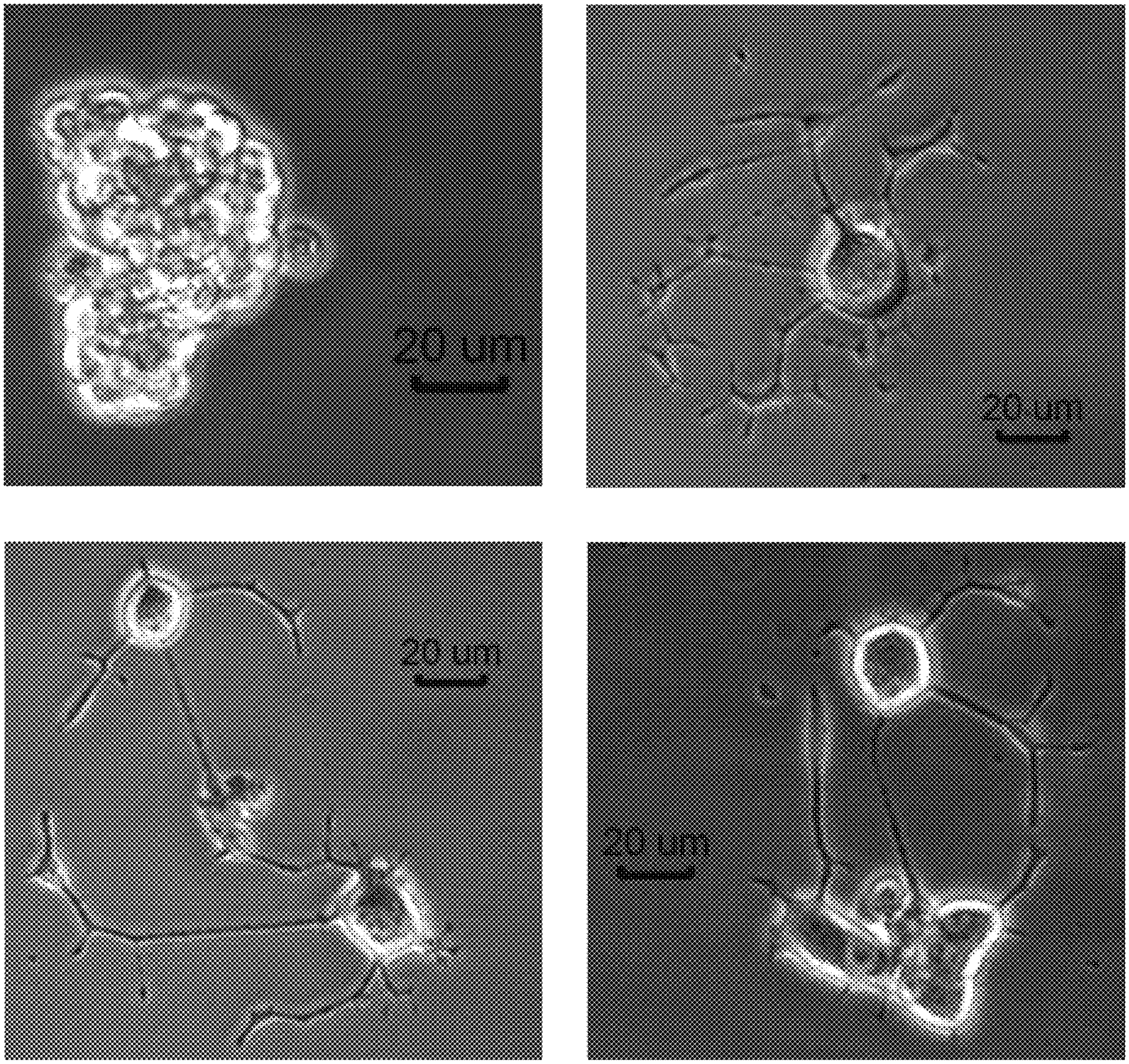
FIG. 10 shows PC12 cell morphology after vehicle vs PACAP treatment (100 nM). Upper Left: diluent only. Upper Right: $PACAP_{1-27}$, Lower Left: $PACAP_{1-27\text{-}S\text{-}G}$, Lower Right: $PACAP_{1-27\text{-}S\text{-}L}$. The cell body volumes all showed increases when treated with each of the PACAP derivatives in Table 1. In all cases the process outgrowths on the treated cells were greater than 2× the cell body width.

Chemical stability of the glycopeptides in vivo clearly plays an important role in the deliverability of the drugs to the site(s) of action within the brain. It is also important to know what the chemical or metabolic instabilities are in order to inform the drug design process. Tandem mass spectroscopy ($MS^n$) was used to determine both the stability of the PACAP compounds in mouse serum, and to identify specific cleavage products, which can stem from inherent chemical instability, or from enzymatic hydrolysis, as shown in FIG. 6 and FIG. 7.

3. $PAC_1$ Agonist Activity of $PACAP_{1-27}$, $PACAP_{6-27}$ and Derivatives, and $PACAP_{1-27\text{-}S\text{-}G}$ Using CHO cells that express human $PAC_1$ receptors, $PACAP_{1-27}$, the glucoside $PACAP_{27\text{-}S\text{-}G}$, and the truncated putative antagonist $PACAP_{6-27}$ and its derivatives were tested as agonists using FLIPR. It was found that $PACAP_{1-27}$ and $PACAP_{1-27\text{-}S\text{-}G}$, the serine glucoside, activated $PAC_1$ with high potency (0.95±0.4 nM and 5.68±2.3 nM respectively, see FIG. 8, Table 2). These values are both very similar to what has been reported for $PACAP_{1-27}$. In addition, the normalized efficacy of the $PACAP_{1-27\text{-}S\text{-}G}$ glucoside was nearly identical to the native $PACAP_{1-27}$ peptide, at 101.9±1.6%. These findings suggest that glycosylation of $PACAP_{1-27}$ does not significantly alter binding and activation of the $PAC_1$ receptor, supporting the use of such a glycopeptide for therapeutic purposes. None of the $PACAP_{6-27}$ derivatives showed agonist activity at concentrations up to 1 μM (see FIG. 8, Table 2).

4. $PAC_1$ Antagonist Activity by PACAP Derivatives

In addition to the agonist studies above, the ability of glycosylated and non-glycosylated $PACAP_{6-27}$ derivatives to block activation of the $PAC_1$ receptor by $PACAP_{1-27}$ was tested. A variable concentration mode antagonist assay was used versus 5 nM of $PACAP_{1-2}$ in the $PAC_1$-CHO cells using FLIPR. Surprisingly, no antagonist activity of $PACAP_{6-27}$ or any derivative up to 1 μM (see FIG. 9, Table 2) was not detected. In addition, the known antagonist $PACAP_{6\_38}$ was tested, and only low potency antagonism was be detected (>333 nM, FIG. 9A and Table 2). These findings are at odds with a molecular pharmacology study of $PACAP_{6-38}$ and $PACAP_{6-27}$ with reported $K_i$ values of 1.5 and 60 nM, respectively (Robberecht et al., Structural requirements for the occupancy of pituitary adenylate-cyclase-activating peptide (PACAP) receptors and adenylate cyclase activation in human neuroblastoma NB-OK-1 cell membranes. Discovery of PACAP6-38 as a potent antagonist. Eur. J. Biochem. 1992, 207, 239-246).

However, one further difference with Robberecht et al. remained, which was the use of fixed concentration antagonist mode experiments. This mode is the most sensitive means of detecting antagonist activity, so experiments were performed using this method with the peptides $PACAP_{6-27}$ and $PACAP_{6-38}$. It was found that $PACAP_{6-27}$ caused no shift in the agonist curves, while $PACAP_{6-38}$ induced a shift only at 1 μM (see FIG. 9B, FIG. 9C, Table 2). This resulted in a pA2 value of 200.6±55.4 nM for $PACAP_{6-38}$, again well above the 1.5 nM value reported by Robberecht. Notably, $PACAP_{6-38}$ also showed a Schild Slope of 2.0±0.1. A Schild Slope of 1 fits the assumptions of the model, while a slope above 1 suggests that the compound is more effective than would be expected for competitive antagonism. This could be due to the short incubation times in the FLIPR assay, which might not be long enough to allow the system to reach equilibrium. The model is only valid at equilibrium. This would result in a high Schild Slope. Alternatively, $PACAP_{6-38}$ could function by a different mechanism, e.g. binding to $VPAC_{1/2}$.

Table 2 shows activity of PACAP derivatives at $PAC_1$. Mean values ±SEM reported, derived from curves in FIGS. 8 and 9. N=3-4 independent experiments. One experiment for $PACAP_{6-38}$ in the Fixed Concentration set could not be fitted to the curves, so N=2 for those values (N=3 for curves in FIG. 9). NC=not converged, no curves could be fit or activity detected. ( )=% inhibition at highest concentration since the curve bottom could not be reliably fit.

TABLE 2

| Agonist Data | Antagonist Data (Variable Concentration) | |
|---|---|---|
| Compound | $EC_{50}$ (nM) | $E_{Max}$ (%) |
| PACAP1-27 | 0.95 ± 0.4 | 100 |
| PACAP1-27-S-G | 5.68 ± 2.3 | 101.9 ± 1.6 |
| PACAP6-27 | NC | |
| PACAP6-27-S-G | NC | |
| PACAP6-27-S-L | NC | |
| PACAP6-27-Alt | NC | |
| PACAP6-27-S-G-Alt | NC | |
| PACAP6-27-S-L-Alt | NC | |
| Antagonist Data (Variable Concentration) | | |
| Compound | $IC_{50}$ (nM) | $I_{Max}$ (%) |
| PACAP6-38 | >333 | (78.8) |
| PACAP6-27 | NC | |
| PACAP6-27-S-G | NC | |
| PACAP6-27-S-L | NC | |
| PACAP6-27-Alt | NC | |
| PACAP6-27-S-G-Alt | NC | |
| PACAP6-27-S-L-Alt | NC | |
| Antagonist Data (Fixed Concentration) | | |
| Compound | pA2 (nM) | Schild Slope |
| PACAP6-38 | 200.6 ± 55.4 | 2.0 ± 0.1 |
| PACAP6-27 | NC | |

5. Differentiation in PC12 Cell Culture

PC12 cells are non-adherent cells, and in spite of using the poly-D-Lysine coated plates, the majority of the cells remained suspended. During the media exchange many of the cells were removed with the spent media. The remaining cells could be visually evaluated for qualitative morphological changes at the end of the treatment period, but meaningful cell quantification could not be done reliably using this approach. It was found that glucoside and lactoside $PACAP_{1-27}$ derivative treatment produced neurite outgrowth and arborization when compared to vehicle treated cells (see FIG. 10). Qualitatively, it appeared that the arborization caused by $PACAP_{1-27}$ may be more extensive than that caused by the glucoside and lactoside derivatives, but again this could not be quantified. In any case, both $PACAP_{1-27}$ and the derivatives induced neurite outgrowth, suggesting native $PAC_1$ agonist activity.

Discussion

Endogenous PACAP peptides occur as C-terminal peptide amides that have either 27 (10%) or 38 (90%) amino acid residues, and are typically regarded as $PAC_1$ agonists in assays using intact tissue or in cell culture. In the present invention, a separate CHO cell line was developed expressing the $PAC_1$ receptor individually. Use of solid-phase peptide synthesis has allowed replacing of the terminal Leucine amide with glycosides of Serine amide bearing the simple sugars glucose or lactose. Notably, these O-linked glycopeptides not only retained their agonist activity on PC12 cell cultures (FIG. 10) and in the quantitative CHO cell assay (FIG. 8 and Table 2), but also showed extended lifetimes in mouse serum (FIG. 7), and provided evidence via microdialysis studies that the glycopeptides can cross the blood brain barrier in mice (FIG. 7).

Given the earlier work of Robberecht, et al. and the widespread acceptance of the truncated peptides $PACAP_{6-38}$ and $PACAP_{6-27}$ as $PAC_1$ antagonists, antagonist activity was expected to be seen in the CHO cell assay with this compound and other truncated peptides. However, the $Ca^{++}$ flux response from the $PAC_1$-CHO cells only showed very weak antagonist activity at $PAC_1$ receptors from $PACAP_{6-38}$, and none by $PACAP_{6-27}$ and derivatives (FIG. 9 and Table 2). It may be worth noting that Robberecht's study is the only molecular pharmacology study of these compounds could be found, with other studies using functional assays like cell growth with endogenous receptor expression or in vivo dosing. Furthermore, Robberecht's study used membranes of neuroblastoma NB-OK-1 cells, which may express other relevant targets besides $PAC_1$ (e.g. $VPAC_1$ and $VPAC_2$). Since the present invention is the only one to inventor's knowledge using isolated $PAC_1$ expression to study receptor function (one earlier Robberecht group study with $PAC_1$ in CHO only studied binding), this raises the possibility that $PACAP_{6-27}$ and $PACAP_{6\_38}$ are not potent antagonists at $PAC_1$ as described, and may prefer other targets. This question has considerable bearing on the potential use of $PACAP_{6-27}$ derivatives as $PAC_1$ antagonists in the treatment of migraine.

Example 2

Example 2 describes the study of glycosides and the Ang-(I-7) peptide. The present invention is not limited to the compounds, configurations, methods, and systems described in Example 2.

Glycosides are added to the aqueous face of the native Ang-(I-7) peptide at (sites on the aqueous surface and not the lipophilic surface). Inherent binding of the glycopeptide to the native receptor is minimally affected. Therefore, the glycosylated Ang-(I-7) derivatives can, at minimum, maintain Mas binding similar to that of the native Ang-(I-7) peptide. Non-limiting examples of Ang-(I-7) derivatives are shown in Table 3.

TABLE 3

| SEQ ID NO: | Ang Peptides | 1 | 2 | 3 | 4 | 5 | 6 | 7 | 8 | |
|---|---|---|---|---|---|---|---|---|---|---|
| 13 | Native $AT_{1-7}$ | Asp | Arg | Val | Tyr | Ile | His | Pro | OH | |
| 14 | ATn-1 | Asp | Arg | Val | Tyr | Ile | His | Pro | $NH_2$ | |
| 15 | ATn-2 | Asp | Arg | Val | Tyr | Ile | His | Pro | Ser ° | $NH_2$ |
| 16 | ATn-3 | Asp | Arg | Val | Tyr | Ile | His | Pro | Ser* | $NH_2$ |
| 17 | ATn-4 | Asp | Arg | Val | Tyr | Ile | His | Pro | Ser** | $NH_2$ |
| 18 | ATn-5 | Asp | Arg | Val | Tyr | Ile | His | Ser* | | |
| | ATn-5-ATN11 | Ala | → | scan | Tyr | Ile | etc . . . | Pro | Ser °/*/** | $NH_2$ |
| 19 | ATn-12 . . . | Asp | Arg | Xxx | Tyr | Yyy | His | Pro | Ser °/*/** | $NH_2$ |
| 20 | ATn-XX . . . | Asp | Arg | Xxx | Zzz | Yyy | His | Pro | Ser °/*/** | $NH_2$ |

The degree of glycosylation (unglycosylated Ser°, glucosylated Ser*' or lactosylated Ser**) for optimal BBB transport is determined using the best binding compounds from these using the in vivo mouse model. Besides the disaccharide β-lactose, the more robust disaccharide β-cellobiose is examined using these structures. An alanine scan will allow for focused attention on the residues most likely to result in increased interaction of the glycopeptides with the Mas receptor (e.g. "hot spots"), and with a glycosylation state most likely to result in penetration of the BBB. Non-peptidic D-amino acids and N-methylated amino acids, as well as un-natural amino acids are substituted at 1-2 of the "hottest spots" to optimize binding (ATn-12 . . . , Table 1). Valine$^3$ and Isoleucine$^5$ have been used here to illustrate the process with Xxx and Yyy to indicated amino acid selection. After optimal substitution is achieved for these positions, an additional round of substitution (Zzz) is done to further optimize binding.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims.

Therefore, the scope of the invention is only to be limited by the following claims.

Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A glycopeptide having at least one pseudoproline residue, wherein the glycopeptide is according to formula 1:

(1)

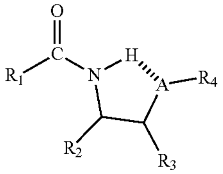

wherein A is an oxygen or a sulfur, $R_1$ is a first peptide chain, $R_2$ is a second peptide chain or —(C═O)$NH_2$, $R_3$ is a hydrogen or methyl, and $R_4$ is a glycoside moiety, wherein the first peptide chain or second peptide chain is an enkephalin, an endorphin, a dynorphin, a pituitary adenvlate cyclase-activatina nolvpentide (PACAP), an endogenous neuroDeDtide, a secretin family peptide, alamandine, or derivatives thereof, wherein the pseudoproline residue is formed by hydrogen bonding of an amino functionality to the A being glycosidically bonded to the glycoside moiety, wherein the glycopeptide has an increased ability to cross a blood brain barrier and an increased half life as compared to a version of the glycosylated peptide lacking a glycosylation.

2. The glycopeptide of claim 1, wherein the glycoside moiety is a saccharide.

3. The glycopeptide of claim 2, wherein the saccharide is a glucose, a maltose, a xylose, a lactose or a cellobiose.

4. The glycopeptide of claim 1, wherein the glycopeptide is amphipathic.

5. The glycopeptide of claim 1, wherein the glycoside moiety effectuates crossing of the glycopeptide by adsorption and desorption from a biological membrane.

6. The glycopeptide of claim 1, wherein the glycopeptide is water-soluble.

7. The glycopeptide of claim 1, wherein the glycopeptide is folded along the peptide side chain, wherein charged groups of the glycopeptide are disposed toward one end of the glycopeptide.

8. The glycopeptide of claim 1, wherein the glycopeptide is helical.

9. A method for synthesizing a glycopeptide having at least one pseudoproline residue, wherein a conformation of the glycopeptide is according to formula 1:

(1)

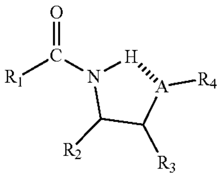

wherein A is an oxygen or a sulfur, $R_1$ is a first peptide chain, $R_2$ is a second peptide chain or —(C═O)$NH_2$, $R_3$ is a hydrogen or methyl, and $R_4$ is a glycoside moiety, said method comprising:

a. synthesizing a glycosidic bond between a saccharide and a reactive functional group of a carrier amino acid to form a glycosylated amino acid, wherein the carrier amino acid comprises A, $R_2$, and $R_3$, wherein the reactive functional group comprises A, and wherein the saccharide comprises $R_4$;

b. incorporating the glycosylated amino acid into an amino acid residue of $R_1$; and c. effecting ring closure by spontaneously forming a hydrogen bond between a hydrogen atom of an amino group of the amino acid residue and the reactive functional group, A, to form a pseudoproline, thereby forming the properly oriented glycosylated peptide, wherein the first peptide chain or second peptide chain is an enkephalin, an endorphin, a dynorphin, a pituitary adenviate cyclase-activating polypeptide (PACAP), an endoaenous neuropeptide, a secretin family peptide, alamandine, or derivatives thereof.

10. The method of claim 9, wherein the carrier amino acid is serine, threonine, cysteine, or extended alkyl derivatives thereof.

11. The method of claim 9, wherein the reactive functional group is an —OH or —SH.

12. The method of claim 9, wherein the saccharide is a glucose, a maltose, a lactose or a cellobiose.

13. The method of claim 9, wherein the glycopeptide is amphipathic.

14. The method of claim 9, wherein the saccharide effectuates crossing of the glycopeptide by adsorption and desorption from a biological membrane.

15. The method of claim 9, wherein the glycopeptide is water-soluble.

16. The method of claim 9, wherein the glycopeptide is folded along the side peptide chain such that charged groups of the glycopeptide are disposed on one end of the glycopeptide.

17. The method of claim 9, wherein the glycopeptide is helical.

18. A composition of a glycopeptide having at least one pseudoproline residue, said composition of the glycopeptide comprising one of the following:

i.

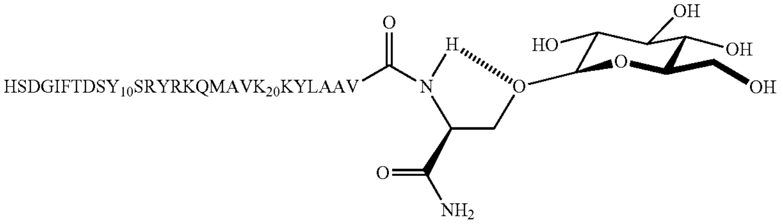

wherein HSDGIFTDSY$_{10}$SRYRKQMAVK$_{20}$KYLAAV=pituitary adenylate cyclase-activating peptide (PACAP$_{1\text{-}26}$) (SEQ ID NO: 10);

ii.

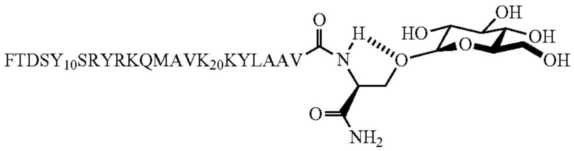

wherein FTDSY$_{10}$SRYRKQMAVK$_{20}$KYLAAV=pituitary adenylate cyclase-activating peptide (PACAP$_{6\text{-}26}$) (SEQ ID NO: 11);

iii.

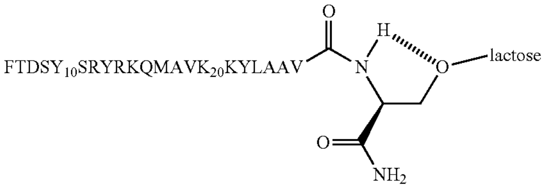

wherein FTDSY$_{10}$SRYRKQMAVK$_{20}$KYLAAV=pituitary adenylate cyclase-activating peptide (PACAP$_{6\text{-}26}$) (SEQ ID NO: 11), and lactose=(-β-D-Glc-β-D-Gal).

* * * * *

UNITED STATES PATENT AND TRADEMARK OFFICE

CERTIFICATE OF CORRECTION

PATENT NO. : 10,858,410 B2
APPLICATION NO. : 15/752157
DATED : December 8, 2020
INVENTOR(S) : Robin L. Polt et al.

It is certified that error appears in the above-identified patent and that said Letters Patent is hereby corrected as shown below:

In the Claims

In Claim 1, Column 31, Lines 32 to 36 should read:
wherein the first peptide chain or second peptide chain is an enkephalin, an endorphin, a dynorphin, a pituitary adenylate cyclase-activating polypeptide (PACAP), an endogenous neuropeptide, a secretin family peptide, alamandine, or derivatives thereof, In Claim 9, Column 32, Lines 40 to 44 should read:
wherein the first peptide chain or second peptide chain is an enkephalin, an endorphin, a dynorphin, a pituitary adenylate cyclase-activating polypeptide (PACAP), an endogenous neuropeptide, a secretin family peptide, alamandine, or derivatives thereof.

In Claim 18, Column 33, Lines 13 to 16 should read:
wherein HSDGIFTDSY10SRYRKQMAVK20KYLAAV = pituitary adenylate cyclase-activating peptide (PACAP1-26) (SEQ ID NO: 10);

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 21

<210> SEQ ID NO 1
<211> LENGTH: 27
<212> TYPE: PRT
<213> ORGANISM: Homo sapiens

<400> SEQUENCE: 1

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25


<210> SEQ ID NO 2
<211> LENGTH: 27
<212> TYPE: PRT
<213> ORGANISM: Artificial Sequence
<220> FEATURE:
<223> OTHER INFORMATION: Modified PACAP peptide
<220> FEATURE:
<221> NAME/KEY: CARBOHYD
<222> LOCATION: (27)..(27)
<223> OTHER INFORMATION: Ser comprises O-linked beta D glucose

<400> SEQUENCE: 2

His Ser Asp Gly Ile Phe Thr Asp Ser Tyr Ser Arg Tyr Arg Lys Gln
1               5                   10                  15

Met Ala Val Lys Lys Tyr Leu Ala Ala Val Ser
            20                  25


<210> SEQ ID NO 3
<211> LENGTH: 22
<212> TYPE: PRT
<213> ORGANISM: Artificial Sequence
<220> FEATURE:
<223> OTHER INFORMATION: Modified PACAP peptide

<400> SEQUENCE: 3

Phe Thr Asp Ser Tyr Ser Arg Tyr Arg Lys Gln Met Ala Val Lys Lys
1               5                   10                  15
```

Tyr Leu Ala Ala Val Leu
20

<210> SEQ ID NO 4
<211> LENGTH: 33
<212> TYPE: PRT
<213> ORGANISM: Artificial Sequence
<220> FEATURE:
<223> OTHER INFORMATION: Modified PACAP peptide

<400> SEQUENCE: 4

Phe Thr Asp Ser Tyr Ser Arg Tyr Arg Lys Gln Met Ala Val Lys Lys
1 5 10 15

Tyr Leu Ala Ala Val Leu Gly Lys Arg Tyr Lys Gln Arg Val Lys Asn
20 25 30

Tyr

<210> SEQ ID NO 5
<211> LENGTH: 22
<212> TYPE: PRT
<213> ORGANISM: Artificial Sequence
<220> FEATURE:
<223> OTHER INFORMATION: Modified PACAP peptide
<220> FEATURE:
<221> NAME/KEY: CARBOHYD
<222> LOCATION: (22)..(22)
<223> OTHER INFORMATION: Ser comprises O-Beta-D glucose

<400> SEQUENCE: 5

Phe Thr Asp Ser Tyr Ser Arg Tyr Arg Lys Gln Met Ala Val Lys Lys
1 5 10 15

Tyr Leu Ala Ala Val Ser
20

<210> SEQ ID NO 6
<211> LENGTH: 22
<212> TYPE: PRT
<213> ORGANISM: Artificial Sequence
<220> FEATURE:
<223> OTHER INFORMATION: Modified PACAP peptide
<220> FEATURE:
<221> NAME/KEY: CARBOHYD
<222> LOCATION: (22)..(22)
<223> OTHER INFORMATION: Ser comprises O-beta-D-glucose-beta-D-galactose

<400> SEQUENCE: 6

Phe Thr Asp Ser Tyr Ser Arg Tyr Arg Lys Gln Met Ala Val Lys Lys
1 5 10 15

Tyr Leu Ala Ala Val Ser
20

<210> SEQ ID NO 7
<211> LENGTH: 22
<212> TYPE: PRT
<213> ORGANISM: Artificial Sequence
<220> FEATURE:
<223> OTHER INFORMATION: Modified PACAP peptide

<400> SEQUENCE: 7

Phe Thr Asp Ser Tyr Ser Arg Tyr Arg Arg Gln Leu Ala Val Arg Arg
1 5 10 15

Tyr Leu Ala Ala Val Leu
20

<210> SEQ ID NO 8

-continued

<211> LENGTH: 22
<212> TYPE: PRT
<213> ORGANISM: Artificial Sequence
<220> FEATURE:
<223> OTHER INFORMATION: Modified PACAP peptide
<220> FEATURE:
<221> NAME/KEY: CARBOHYD
<222> LOCATION: (22)..(22)
<223> OTHER INFORMATION: Ser comprises O-beta-D-Glucose

<400> SEQUENCE: 8

```
Phe Thr Asp Ser Tyr Ser Arg Tyr Arg Arg Gln Leu Ala Val Arg Arg
1               5                   10                  15

Tyr Leu Ala Ala Val Ser
            20
```

<210> SEQ ID NO 9
<211> LENGTH: 22
<212> TYPE: PRT
<213> ORGANISM: Artificial Sequence
<220> FEATURE:
<223> OTHER INFORMATION: Modified PACAP peptide
<220> FEATURE:
<221> NAME/KEY: CARBOHYD
<222> LOCATION: (22)..(22)
<223> OTHER INFORMATION: Ser comprises O-beta-D-glc-beta-D-gal

<400> SEQUENCE: 9

```
Phe Thr Asp Ser Tyr Ser Arg Tyr Arg Arg Gln Leu Ala Val Arg Arg
1               5                   10                  15

Tyr Leu Ala Ala Val Ser
            20
```

<210> SEQ ID NO 10
<211> LENGTH: 26
<212> TYPE: PRT
<213> ORGANISM: Homo sapiens

<400> SEQUENCE: 10

```
His Ser Asp Gly Ile Phe Thr Asp Ser Tyr Ser Arg Tyr Arg Lys Gln
1               5                   10                  15

Met Ala Val Lys Lys Tyr Leu Ala Ala Val
            20                  25
```

<210> SEQ ID NO 11
<211> LENGTH: 21
<212> TYPE: PRT
<213> ORGANISM: Homo sapiens

<400> SEQUENCE: 11

```
Phe Thr Asp Ser Tyr Ser Arg Tyr Arg Lys Gln Met Ala Val Lys Lys
1               5                   10                  15

Tyr Leu Ala Ala Val
            20
```

<210> SEQ ID NO 12
<211> LENGTH: 6
<212> TYPE: PRT
<213> ORGANISM: Homo sapiens

<400> SEQUENCE: 12

```
Asp Arg Val Tyr Ile His
1               5
```

<210> SEQ ID NO 13

-continued

<211> LENGTH: 7
<212> TYPE: PRT
<213> ORGANISM: Homo sapiens

<400> SEQUENCE: 13

Asp Arg Val Tyr Ile His Pro
1 5

<210> SEQ ID NO 14
<211> LENGTH: 7
<212> TYPE: PRT
<213> ORGANISM: Artificial Sequence
<220> FEATURE:
<223> OTHER INFORMATION: Modified angiotensin peptide
<220> FEATURE:
<221> NAME/KEY: MOD_RES
<222> LOCATION: (7)..(7)
<223> OTHER INFORMATION: Pro comprises terminal amine

<400> SEQUENCE: 14

Asp Arg Val Tyr Ile His Pro
1 5

<210> SEQ ID NO 15
<211> LENGTH: 8
<212> TYPE: PRT
<213> ORGANISM: Artificial Sequence
<220> FEATURE:
<223> OTHER INFORMATION: Modified angiotensin peptide
<220> FEATURE:
<221> NAME/KEY: MOD_RES
<222> LOCATION: (8)..(8)
<223> OTHER INFORMATION: Ser comprises terminal amine

<400> SEQUENCE: 15

Asp Arg Val Tyr Ile His Pro Ser
1 5

<210> SEQ ID NO 16
<211> LENGTH: 8
<212> TYPE: PRT
<213> ORGANISM: Artificial Sequence
<220> FEATURE:
<223> OTHER INFORMATION: Modified angiotensin peptide
<220> FEATURE:
<221> NAME/KEY: MOD_RES
<222> LOCATION: (8)..(8)
<223> OTHER INFORMATION: Ser comprises glucosylated Ser and terminal amine

<400> SEQUENCE: 16

Asp Arg Val Tyr Ile His Pro Ser
1 5

<210> SEQ ID NO 17
<211> LENGTH: 8
<212> TYPE: PRT
<213> ORGANISM: Artificial Sequence
<220> FEATURE:
<223> OTHER INFORMATION: Modified angiotensin peptide
<220> FEATURE:
<221> NAME/KEY: MOD_RES
<222> LOCATION: (8)..(8)
<223> OTHER INFORMATION: Ser comprises lactosylated Ser and terminal amine

<400> SEQUENCE: 17

Asp Arg Val Tyr Ile His Pro Ser
1 5

<210> SEQ ID NO 18
<211> LENGTH: 7
<212> TYPE: PRT
<213> ORGANISM: Artificial Sequence
<220> FEATURE:
<223> OTHER INFORMATION: Modified angiotensin peptide
<220> FEATURE:
<221> NAME/KEY: MOD_RES
<222> LOCATION: (7)..(7)
<223> OTHER INFORMATION: Ser comprises glucosylated Ser

<400> SEQUENCE: 18

Asp Arg Val Tyr Ile His Ser
1               5

<210> SEQ ID NO 19
<211> LENGTH: 8
<212> TYPE: PRT
<213> ORGANISM: Artificial Sequence
<220> FEATURE:
<223> OTHER INFORMATION: Modified angiotensin peptide
<220> FEATURE:
<221> NAME/KEY: MISC_FEATURE
<222> LOCATION: (3)..(3)
<223> OTHER INFORMATION: Xaa can be any naturally occurring amino acid, un-natural amino acids, non-peptidic D-amino acids, or N-methylated amino acids
<220> FEATURE:
<221> NAME/KEY: MISC_FEATURE
<222> LOCATION: (5)..(5)
<223> OTHER INFORMATION: Xaa can be any naturally occurring amino acid, un-natural amino acids, non-peptidic D-amino acids, or N-methylated amino acids
<220> FEATURE:
<221> NAME/KEY: MOD_RES
<222> LOCATION: (8)..(8)
<223> OTHER INFORMATION: Ser could be unglycosylated, glucosylated, or lactosylated; Ser comprises terminal amine

<400> SEQUENCE: 19

Asp Arg Xaa Tyr Xaa His Pro Ser
1               5

<210> SEQ ID NO 20
<211> LENGTH: 8
<212> TYPE: PRT
<213> ORGANISM: Artificial Sequence
<220> FEATURE:
<223> OTHER INFORMATION: Modified angiotensin peptide
<220> FEATURE:
<221> NAME/KEY: MISC_FEATURE
<222> LOCATION: (3)..(5)
<223> OTHER INFORMATION: Xaa can be any naturally occurring amino acid, un-natural amino acids, non-peptidic D-amino acids, or N-methylated amino acids
<220> FEATURE:
<221> NAME/KEY: MOD_RES
<222> LOCATION: (8)..(8)
<223> OTHER INFORMATION: Ser could be unglycosylated, glucosylated, or lactosylated; Ser comprises terminal amine

<400> SEQUENCE: 20

Asp Arg Xaa Xaa Xaa His Pro Ser
1               5

<210> SEQ ID NO 21
<211> LENGTH: 7
<212> TYPE: PRT
<213> ORGANISM: Artificial Sequence
<220> FEATURE:
<223> OTHER INFORMATION: Modified angiotensin peptide
<220> FEATURE:

-continued

<221> NAME/KEY: MOD_RES
<222> LOCATION: (7)..(7)
<223> OTHER INFORMATION: Ser could be glucosylated or lactosylated; Ser comprises terminal amine

<400> SEQUENCE: 21

Ala Arg Val Tyr Ile His Ser
1 5